United States Patent [19]
Kroll et al.

[11] Patent Number: 5,405,363
[45] Date of Patent: Apr. 11, 1995

[54] IMPLANTABLE CARDIOVERTER DEFIBRILLATOR HAVING A SMALLER DISPLACEMENT VOLUME

[75] Inventors: Mark W. Kroll, Minnetonka; Theodore P. Adams, Edina; Kenneth M. Anderson, Bloomington; Charles U. Smith, Minnetonka, all of Minn.

[73] Assignee: Angeion Corporation, Plymouth, Minn.

[21] Appl. No.: 263,257

[22] Filed: Jun. 21, 1994

Related U.S. Application Data

[63] Continuation of Ser. No. 33,632, Mar. 15, 1993, abandoned, which is a continuation-in-part of Ser. No. 910,611, Jul. 8, 1992, Pat. No. 5,241,960, and a continuation-in-part of Ser. No. 835,836, Feb. 18, 1992, and a continuation-in-part of Ser. No. 953,485, Sep. 29, 1992, and a continuation-in-part of Ser. No. 808,722, Dec. 17, 1991, Pat. No. 5,342,399, and a continuation-in-part of Ser. No. 989,532, Dec. 11, 1992, and a continuation-in-part of Ser. No. 993,094, Dec. 18, 1992, and a continuation-in-part of Ser. No. 993,292, Dec. 18, 1992, and a continuation-in-part of Ser. No. 913,626, Jul. 16, 1992, Pat. No. 5,235,979, which is a continuation of Ser. No. 670,188, Mar. 15, 1991, abandoned.

[51] Int. Cl.⁶ ............................................. A61N 1/39
[52] U.S. Cl. ............................................ 607/5; 607/36
[58] Field of Search ............................... 607/5, 34, 36

[56] References Cited
FOREIGN PATENT DOCUMENTS
0272021 7/1964 Australia .................. 128/419 D

OTHER PUBLICATIONS

Cardiac Pacemaker, Inc., St. Paul, Minn.; Model 1700.
Ventritex, Sunnyvale, Calif.; "Cadence" tiered therapy defibrillator Model V-100.
Cardiac Pacemakers, Inc., St. Paul, Minn; Ventak Acid, cardioverter defibrillator Models 1500, 1510, 1520.
Medtronic, Inc., "Tachyarrhythmia Management", 1991, Annual Report 1991, pp. 12, 13.
Telectronics Pacing Systems, Inc., "Gaurdian ATP", 1990, Product Brochure, p. 1.
Cardiac Pacemakers, Inc., "Advanced Acid Therapy Made Easy", 1991, Product Brochure, pp. 1, 2.
Hook et al., Advances in Third-Generation ICD Therapy, Cardio, Nov. 1991 pp. 66–72.
Hammel et al., Implantation of a Cardioverter/Defibrillator in Subpectoral Region Combined with a Nonthoracotomy Lead System, Pace, vol. 15, Apr. 1992, pp. 367–368.

(List continued on next page.)

Primary Examiner—George Manuel
Attorney, Agent, or Firm—Patterson & Keough

[57] ABSTRACT

A capacitor-discharge implantable cardioverter defibrillator (ICD) has a relatively smaller displacement volume of less than about 90 cc. The smaller volume of the ICD is achieved by selecting and arranging the internal components of the ICD to deliver a maximum defibrillation countershock optimized in terms of a minimum physiologically effective current ($I_{pe}$), rather than a minimum defibrillation threshold energy (DFT). As a result of the optimization in terms of a minimum effective current $I_{pe}$, there is a significant decrease in the maximum electrical charge energy ($E_c$) that must be stored by the capacitor of the ICD to less than about 30 Joules, even though a higher safety margin is provided for by the device. Due to this decrease in the maximum $E_c$, as well as corollary decreases in the effective capacitance value required for the capacitor and the net energy storage required of the battery, the overall displacement volume of the ICD is reduced to the point where subcutaneous implantation of the device in the pectoral region of human patients is practical. The size of the capacitor is reduced because the effective capacitance required can be less than about 125 μF. By optimizing both the charging time and the countershock duration for the smaller maximum $E_c$, the size of the battery is reduced because the total energy storage capacity can be less than about 1.0 Amp-hours. In the preferred embodiment, the charging time for each defibrillation countershock is reduced to less than about 10 seconds and the pulse duration of the countershock is reduced to less than about 6 milliseconds.

38 Claims, 10 Drawing Sheets

OTHER PUBLICATIONS

The PCD Tachyarrhythmia Control Device, Model 7217B. Device for the control of Ventricular Arrhythmias Through Pacing, Cardioversion and Defibrillation, Medtronic, Inc. Mar., 1990.

M J Niebauer, C F Babbs, L A Geddes, et al, "Efficacy and safety of defibrillation with rectangular waves of 2 to 20-milliseconds duration," *Crit. Care Medicine*, vol. 11 #2, pp. 95–98, Feb. 1983.

S A Feeser, A S L Tang, K M Kavanagh, et al, "Strength-duration and probability of success curves for defibrillation with biphasic waveforms," *Circulation*, vol. 82, pp. 2128–2141, Dec. 1990.

G Koning, H Schneider, A J Hoelen, et al, "Amplitude-duration relation for direct ventricular defibrillation with rectangular current pulses," *Med Biol Eng*, vol. 13, pp. 388–395, May 1975.

J H Gold, J C Schuder, H Stoeckle, et al, "Transthoracic ventricular defibrillation in the 100 Kg calf with unidirectional rectangular pulses," *Circulation*, vol. 56 #5, pp. 745–750, Nov. 1977.

J L Wessale, J D Bourland, W A Tacker, et al, "Bipolar catheter defibrillation in dogs using trapezoidal waveforms of various tilts," *J Electrocardiology*, vol. 13(4), pp. 359–366, 1980.

J L Jones and R E Jones, "Determination of safety factor for defibrillator waveforms in cultured heart cells," *Am J Physiol*, vol. 242, pp. H662–H670, 1982.

M S Chang, H Inoue, M J Kallok, et al, "Double and triple sequential shocks reduce ventricular defibrillation threshold in dogs with and without myocardial infarction," *J Am. Coll. Cardiol.*, vol. 8 #6, pp. 1393–1405, Dec. 1986.

D L Jones, G J Klein, G M Guiraudon, "Internal cardiac defibrillation in man: pronounced improvement with sequential pulse delivery to two different orientations," *Circulation*, vol. 73 #3, pp. 484–491, Mar. 1986.

C F Babbs and S J Whistler, "Evaluation of the operating internal resistance, inductance, and capacitance of intact damped sine wave defibrillators," *Medical Instrum.*, vol. 12 3 1, pp. 34–37, Jan.–Feb. 1978.

R S MacKay and S E Leeds, "Physiological effects of condenser discharges with application to tissue stimulation and ventricular defibrillation," *J Applies Physiology*, vol. 6, pp. 67–75, Jul. 1953.

W B Kouwenhoven and W R Milnor, "Treatment of ventricular fibrillation using a capacitor discharge," *J Applies Physiology*, vol. 7, pp. 253–257, Nov. 1957.

L A Geddes, M J Niebauer, C F Babbs, et al, "Fundamental criteria underlying the efficacy and safety of defibrillating current waveforms," *Med. Biol. Eng. Comp.* vol. 23, pp. 122–130, 1985.

R C Balagot, W S Druz, M Ramadan, et al, "A monopulse DC current defibrillator for ventricular defibrillation," *J Thoracic and Cardiovasc. Surgery*, vol. 47 #4, pp. 487–504, Apr. 1964.

P S Chen, N Shibata, E G Dixon, et al, "Comparison of the defibrillation threshold and the upper limit of ventricular vulnerability," *Circulation*, vol. 73 #5, pp. 102–1028, May 1986.

D. Lang, et al., Proc. Ann. Int. Conf. IEEE Engineer. Med. Biol. Soc., vol. 11: 80–81 (1989).

J A Pearce, J D Bourland, W Neilsen, et al, "Myocardial stimulation with ultrashort duration current pulses," *PACE*, vol. 5 pp. 52–58, Jan.–Feb. 1982.

D S Echt, et al., *Circulation*, vol. 71, No. 2: 289–296 (Feb. 1985).

Rattes et al., American Heart Journal, vol. 111, No. 5, pp. 874–878 (1986).

Kallok et al., Medical Instruments, vol. 20, No. 1, pp. 36–39 (1986).

Kallok et al., Am. Heart J., vol. 109, No. 4, pp. 821–826 (1986).

Jones et al., Circulation, vol. 73, No. 3, pp. 484–491 (1986).

Chang et al., JACC, vol. 8, No. 6, 1393–1405 (1986).

Lang et al., IEEE Engineering in Medicine and Biology Society, vol. 11: 1989.

Yee et al., Can. J. Cardiol., vol. 6, No. 4, pp. 147–156 (1990).

Hammel et al., Pace, vol. 15, pp. 367–368 (1992).

Nedtronic Technical Manual, The PCD. Tacharrythmia Control Device Model 7217B.

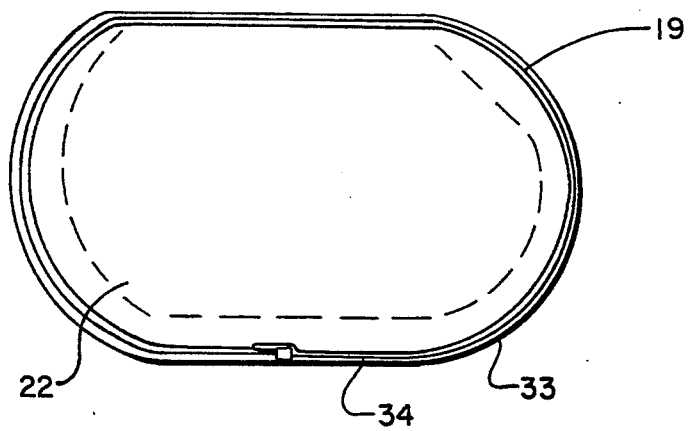
Fig. 6
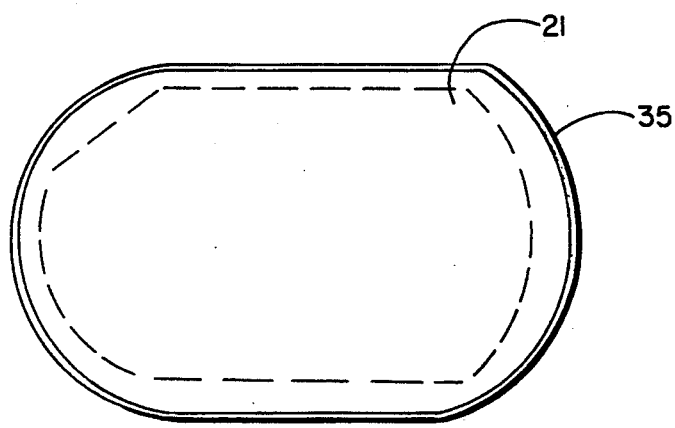
Fig. 7
Fig. 8
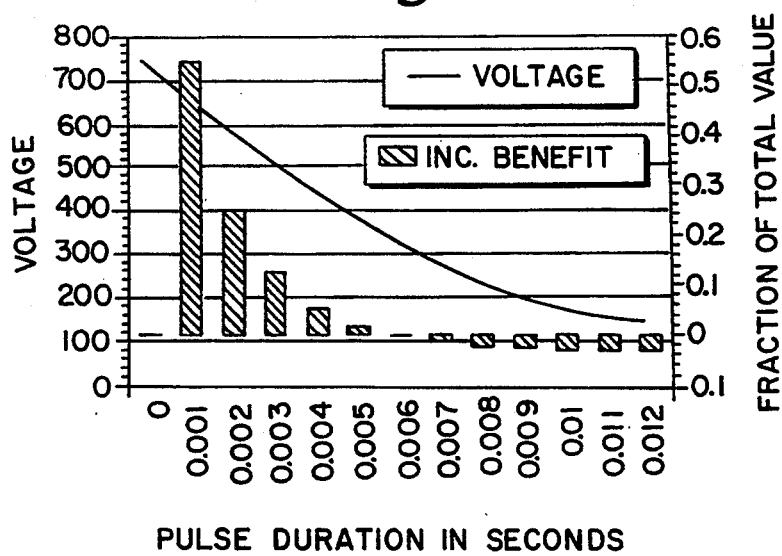
PULSE DURATION IN SECONDS

Fig. 9
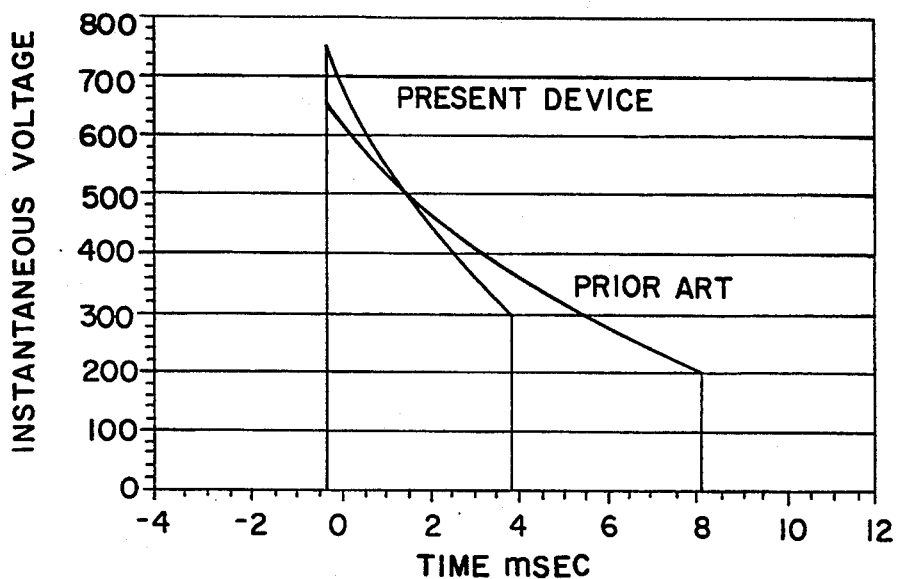
Fig. 10
| | CAPACITOR | VOLTS | Ec | Edel | Ipe | Ipec |
|---|---|---|---|---|---|---|
| PRESENT TWICE | 85μF | 750 | 26J | 25.33J | 5.67A | 7.32A |
| PRIOR ART | 140μF | 750 | 39.4J | 34.0J | 6.79A | 6.79A |
Fig. 11
PRIOR ART
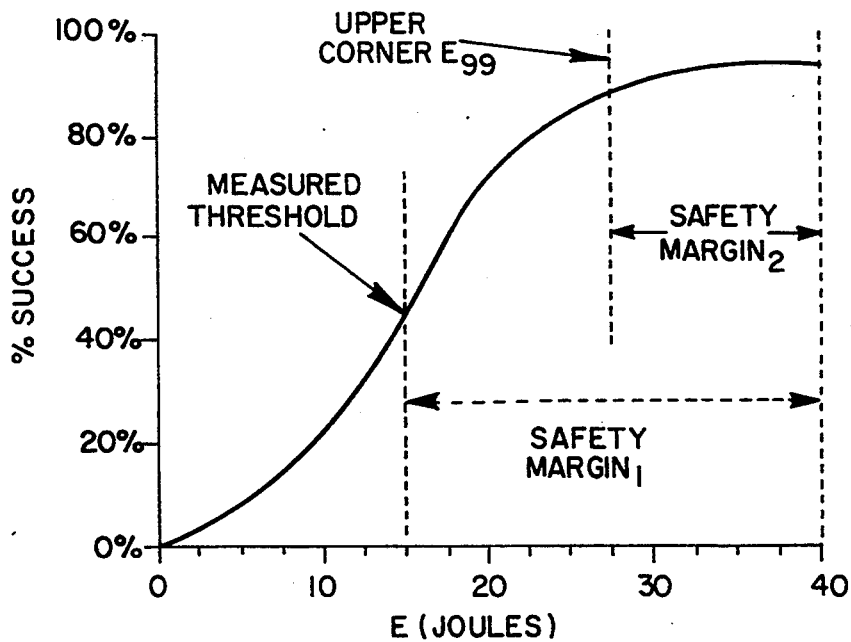

IMPLANTABLE CARDIOVERTER DEFIBRILLATOR HAVING A SMALLER DISPLACEMENT VOLUME

RELATED APPLICATIONS

This application is a continuation of U.S. patent application Ser. No. 08/033,632, filed Mar. 15, 1993, now abandoned, which is a continuation-in-part of the following co-pending applications, each of which are assigned to the assignee of the present invention, the disclosure of each of which is hereby incorporated by reference in this application:

U.S. patent application Ser. No. 07/910,611, filed July 8, 1992, now U.S. Pat. No. 5,241,960, entitled "DEFIBRILLATOR PULSE GENERATOR";

U.S. patent application Ser. No. 07/835,836, filed Feb. 18, 1992, entitled "OPTIMAL PULSE DEFIBRILLATION METHOD AND IMPLANTABLE SYSTEMS";

U.S. patent application Ser. No. 07/953,485, filed Sep. 29, 1992, entitled "SHORT-PULSE IMPLANTABLE DEFIBRILLATION SYSTEMS";

U.S. patent application Ser. No. 07/808,722, filed Dec. 17, 1991, now U.S. Pat. No. 5,342,399, entitled "SMALL-CAPACITANCE DEFIBRILLATION PROCESS";

U.S. patent application Ser. No. 07/989,532, filed Dec. 11, 1992, entitled "PROCESS AND APPARATUS FOR A DEFIBRILLATION SYSTEM WITH A SMALL CAPACITOR";

U.S. patent application Ser. No. 07/913,626, filed Jul. 16, 1992, now U.S. Pat. No. 5,235,979, as a continuation of U.S. patent application Ser. No. 07/670,188, filed Mar. 15, 1991, now abandoned and entitled "DUAL BATTERY SYSTEM FOR IMPLANTABLE DEFIBRILLATORS";

U.S. patent application Ser. No. 07/993,094, filed Dec. 18, 1992, entitled "STAGED ENERGY CONCENTRATION FOR A DEFIBRILLATOR"; and U.S. patent application Ser. No. 07/993,292, filed Dec. 18, 1992, entitled "SYSTEM AND METHOD FOR DELIVERING MULTIPLE CLOSELY SPACED DEFIBRILLATION PULSES".

TECHNICAL FIELD

The present invention relates generally to the field of automatic, implantable cardioverters and defibrillators. More particularly, the present invention relates to an implantable cardioverter defibrillator (ICD) that is a capacitor-discharge device having its internal components, including a battery and a capacitor, selected and arranged in such a manner that the ICD has a relatively smaller displacement volume that permits effective subcutaneous implantation of the device in the pectoral region of human patients.

BACKGROUND OF THE INVENTION

Existing implantable cardioverter defibrillators (ICDs) are typified by a relatively large size that usually requires implantation of the prosthetic device in the abdominal cavity of a human patient. In order to allow for effective subcutaneous implantation of a prosthetic device in the pectoral region of a human patient, the maximum size of the prosthetic device needs to be less than about 40-90 cc, depending upon the physical size and weight of the patient. Unfortunately, all existing ICDs have total displacement volumes of at least 110 cc or greater. Even though there are numerous advantages to developing an ICD having a displacement volume small enough to permit implantation of the device in the pectoral region of a human patient, to date it has been difficult to develop a practical ICD having a total displacement volume of less than about 100 cc.

For reasons of simplicity and compactness, existing ICDs are universally capacitors-discharge systems that generate high energy cardioversion/defibrillation countershocks by using a low voltage battery to charge a capacitor over a relatively long time period (i.e., seconds) with the required energy for the defibrillation countershock. Once charged, the capacitor is then discharged for a relatively short, truncated time period (i.e., milliseconds) at a relatively high discharge voltage to create the defibrillation countershock that is delivered through implantable electrode leads to the heart muscle of the human patient.

One of the primary reasons why capacitor-discharge ICDs of a smaller volume have not been developed to date relates to the electrical requirements for storing the high energy cardioversion/defibrillation countershocks that are currently used to defibrillate human patients. Cardioversion countershocks have delivered energies of between about 0.5 to 5.0 Joules and are used to correct detected arrhythmias, such as tachycardia, before the onset of fibrillation. Defibrillation countershocks, on the other hand, have delivered energies greater than about 3.0 Joules and are use to correct ventricular fibrillation or an advanced arrhythmia condition that has not responded to cardioversion therapy.

Presently, all capacitor-discharge ICDs are designed such that the capacitor can store a maximum electrical charge energy of at least about 35 Joules. In contrast, implantable pacemakers, which currently have displacement volumes of less than 50 cc, are designed to deliver pacing pulses of no more than about 50 $\mu$Joules. The requirement that a capacitor-discharge ICD be capable of storing an electrical charge with enough energy to deliver an electrical pulse almost one million times as large as that of an implantable pacemaker significantly increases the size of the ICD over the size of the pacemaker due to the size of the electrical components necessary to store this amount of electrical charge energy.

The accepted requirement that ICDs be capable of storing a maximum electrical charge energy of at least about 35 Joules arises out of the definition of an appropriate safety margin for the device according to a clinically developed defibrillation success curve as shown in FIG. 11. The defibrillation success curve plots the percentage probability of successful defibrillation for a ventricular fibrillation of about 5–10 seconds versus the energy of a monophasic defibrillation countershock as measured in Joules. The safety margin for a given device for a given patient is presently accepted to be the difference between the maximum electrical charge energy ($E_c$) stored by the capacitor in that device and the median defibrillation threshold energy (DFT) required for that patient.

Under existing medical practice, each time an ICD is implanted in a human patient, an intraoperative testing procedure is attempted in order to determine the median DFT for that patient for the particular electrode lead combination which has been implanted in the patient. The intraoperative testing procedure involves inducing ventricular fibrillation in the heart and then immediately delivering a defibrillation countershock through the implanted electrode leads of a specified initial threshold energy, for example, 20 Joules for a monophasic countershock. If defibrillation is successful, a recovery period is provided for the patient and the procedure is usually repeated a small number of times using successively lower threshold energies until the defibrillation countershock is not successful or the threshold energy is lower than about 10 Joules. If defibrillation is not successful, subsequent countershocks of 35 Joules or more are immediately delivered to resuscitate the patient. After a recovery period, the procedure is repeated using a higher initial threshold energy, for example, 25 Joules. It is also possible that during the recovery period prior to attempting a higher initial threshold energy, the electrophysiologist may attempt to lower the DFT for that patient by moving or changing the electrode leads.

The intraoperative testing procedure is designed to accomplish a number of objectives, including patient screening and establishing a minimum DFT for that patient. Typically, if more than 30–35 Joules are required for successful defibrillation with a monophasic countershock, the patient is not considered to be a good candidate for an ICD and alternative treatments are used. Otherwise, the lowest energy countershock that results in successful defibrillation is considered to be the median DFT for that patient. The use of the lowest energy possible for a defibrillation countershock is premised on the accepted guideline that a countershock which can defibrillate at a lower energy decreases the likelihood of damage to the myocardial tissue of the heart. For a background on current intraoperative testing procedures, reference is made to M. Block, et al., "Intraoperative Testing for Defibrillator Implantation", Chpt. 3; and J. M. Almendral, et al., "Intraoperative Testing for Defibrillator Implantation", Chpt. 4, *Practical Aspects of Staged Therapy Defibrillators*, edited by Kappenberger, L. J. and Lindemans, F. W., Futura Publ. Inc., Mount Kisco, N.Y. (1992), pgs. 11–21.

Once the median DFT for a patient is established, the electrophysiologist will determine a safety margin for a given ICD device usually by subtracting the median DFT from the maximum $E_c$ stored by that device. Alternatively, a different calculation for the safety margin is sometimes determined by estimating that point on the defibrillation success curve where the electrical energy of a defibrillation countershock will insure a 99% success ($E_{99}$). Under either definition, the safety margin needs to be large enough to accommodate upward deviations along the defibrillation success curve. Such deviations may be expected, for example, with subsequent rescue defibrillation countershocks delivered later in a treatment after initial cardioversion or defibrillation countershocks of lesser energies were not successful. In these situations clinical data has found that, when delivered after 30 to 40 seconds of ventricular fibrillation, the electrical energy necessary to achieve effective defibrillation may increase 50% or more over the median DFT. As a result, an electrophysiologist usually will require that a given ICD have a first type of safety margin that is typically a factor of at least 2 to 2.5 times the median DFT for that patient before the electrophysiologist will consider implanting the given ICD in that patient. For the alternate $E_{99}$ point safety margin, the electrophysiologist will require that a given ICD have a maximum $E_c$ at least 10 Joules above the $E_{99}$ point.

Based on current clinical data that the average median DFT is somewhere between 10–20 Joules for a monophasic countershock, the lower limit for the maximum $E_c$ that must be stored by the ICD is accepted to be at least about 35 Joules, and more typically about 39 Joules, in order to generate a maximum defibrillation countershock having an adequate safety margin. The accepted lower limit for the maximum $E_c$ of at least 35 Joules is supported by clinical evaluations, such as Echt, D. S., et al., "Clinical Experience, Complications, and Survival in 70 Patients with the Automatic Implantable Cardioverter/Defibrillator", *Circulation*, Vol. 71, No. 2:289–296, Feb. 1985. In this article, the authors evaluated data for early AICD devices having maximum $E_c$ energies of 32 Joules stored in a 120 $\mu$LF capacitor with a discharge voltage $V_d$ of 750 Volts. In analyzing the clinical data for minimum DFTs, the authors concluded that the 32 Joule device had insufficient energy for effective defibrillation. It should be noted that in the next generation of the particular AICD devices studied, the maximum $E_c$ for the device (the CPI Ventak ®) was increased to 39.4 Joules by increasing the capacitance value of the ICD by using a 140 $\mu$F capacitor.

Unfortunately, the requirement that an ICD be capable of storing a maximum $E_c$ of this magnitude effectively dictates that the size of the ICD be greater than about 100 cc. This relationship between the maximum $E_c$ that is required for an ICD and the overall size of the ICD can be understood by examining how an ICD stores the electrical energy necessary to deliver a maximum defibrillation countershock.

The only two components that impact on the ability of a capacitor-discharge ICD to store a maximum $E_c$ are the capacitor and the battery, which together occupy more than 60% of the total displacement volume of existing ICDs. Thus, it will be apparent that the size of a capacitor-discharge ICD is primarily a function of the size of the capacitor and the size of the battery. For a capacitor, the physical size of that capacitor is principally determined by its capacitance and voltage ratings. The higher the capacitance value, the larger the capacitor. Similarly, the physical size of a battery is also principally determined by its total energy storage, as expressed in terms of Amp-hours, for example. Again, the higher the Amp-hours, the larger the battery. With these concepts in mind, it is possible to evaluate how a maximum $E_c$ affects the size of the capacitor and the size of the battery in an ICD.

The maximum electrical charge energy ($E_c$) of an ICD is usually defined in terms of the capacitance value (C) of the capacitor that stores the charge and the discharge voltage ($V_d$) at which the electrical charge is delivered as defined by the equation:

$$E_c = 0.5 * C * V_d^2 \tag{Eq. 1}$$

The maximum electrical charge energy ($E_c$) can also be defined in terms of how the energy is transferred from the battery to the capacitor. In this case, $E_c$ is determined by the charging efficiency ($e_c$) of the circuitry charging the capacitor, the battery voltage ($V_b$), the battery current ($I_b$) and the charging time (tc) as defined by the equation:

$$E_c = e_c * V_b * I_b * t_c \tag{Eq. 2}$$

When Eqs. 1 and 2 are used to calculate a maximum $E_c$ to be stored by the device, the capacitance value (C) and the charging time ($t_c$) end up being the only true variables in these equations because the remaining values are all effectively determined by other constraints. In Eq. 1, for example, the discharge voltage ($V_d$) for present ICDs can be no more than about 800 Volts due to voltage breakdown limitations of high power microelectronic switching components. As a result, V d is typically between 650-750 Volts. In Eq. 2, it will be found that, for batteries suitable for use in an ICD, the maximum battery output voltage ($V_b$) for ICDs is typically less than 6 Volts and, due to internal impedances within these batteries, the maximum battery current ($I_b$) is about 1 Amp. In addition, the charging efficiencies ($e_c$) of existing ICDs are presently on the order of about 50%.

When Eqs. 1 and 2 are evaluated for any given maximum $E_c$, it will be found that there necessarily is a minimum capacitance value ($C_{min}$) for the capacitor and a minimum charging time ($t_{min}$) required to store that maximum $E_c$ in the capacitor of the ICD. Knowing $E_c$ and $V_d$, Eq. I can be reworked as follows to solve for $C_{min}$:

$$C_{min} = 2E_c/V_d^2 \quad \text{(Eq. 3)}$$
$$= 2 * 35 \text{ Joules}/(750 \text{ Volts})^2$$
$$= 124.4 \ \mu F$$

Similarly, knowing $E_c$, $V_b$, $I_b$, and e, Eq. 2 can be reworked as follows to solve for $t_{min}$:

$$t_{min} = E_c/(e * V_b * I_b) \quad \text{(Eq. 4)}$$
$$= (35 \text{ Joules})/((0.50) * (6 \text{ Volts}) * (1 \text{ Amp}))$$
$$= 12 \text{ seconds}$$

In other words, the fact that all ICDs presently use a maximum $E_c$ of at least 35 Joules means that all existing ICDs will require capacitors of greater than 124 $\mu F$, and that all existing ICDs which draw 1 Amp of current from the battery will have a charging time of greater than 12 seconds. Because the physical size of the capacitor is directly proportional to the capacitance rating of the capacitor in farads for a fixed voltage, the requirement that the capacitor be at least 124 $\mu F$ is effectively a minimum size limitation on the capacitor for discharge voltages of less than about 800 Volts. Similarly, the requirement that each charging time for a defibrillation countershock draw at least 12 Ampseconds of current from the battery is also a constructive minimum size limitation on the battery. Thus, it can be seen that the existing requirement for a maximum $E_c$ of at least about 35 Joules effectively dictates the size of both the capacitor and the battery and, consequently, the size of the ICD.

While existing ICDs have been successful in defibrillating human patients, and thereby saving lives, these devices are primarily limited to implantation in the abdominal cavity due to their relatively large size of greater than 110 cc. It has long been recognized that it would be advantageous to reduce the total displacement volume of an ICD sufficiently to allow for subcutaneous implantation of the device in the pectoral region of human patients. This can only be done, however, so long as the device provides for a sufficient safety margin to insure its effectiveness. Accordingly, it would be desirable to provide for an arrangement and configuration of the internal components of a capacitor-discharge ICD such that the total displacement volume of the ICD is reduced, while a sufficient safety margin for the device is retained.

SUMMARY OF THE INVENTION

The present invention is a capacitor-discharge implantable cardioverter defibrillator (ICD) having a relatively smaller displacement volume of less than about 90 cc that permits effective subcutaneous implantation of the device in the pectoral region of human patients. The smaller volume of the ICD of the present invention is achieved by selecting and arranging the internal components of the capacitor-discharge ICD in such a manner that the ICD delivers a maximum defibrillation countershock optimized in terms of a minimum physiologically effective current ($I_{pe}$), rather than a minimum defibrillation threshold energy (DFT). One of the important results of optimizing the maximum defibrillation countershock in terms of a minimum effective current $I_{pe}$ is that there is a significant decrease in the maximum electrical charge energy ($E_c$) that must be stored by the capacitor of the ICD to less than about 30 Joules, even though a higher safety margin is provided for by the ICD. Due to this decrease in the maximum $E_c$, as well as corollary decreases in the effective capacitance value required for the capacitor and the net energy storage required of the battery, the overall displacement volume of the ICD of the present invention is reduced to the point where subcutaneous implantation of the device in the pectoral region of human patients is practical.

By using a physiologically effective current ($I_{pe}$) to determine what is a safe and effective maximum defibrillation countershock, the present invention takes advantages of the realization that it is the effective current delivered to the heart by the defibrillation countershock, and not the total energy of the defibrillation countershock, that results in effective defibrillation. In other words, the present invention recognizes that all Joules are not created equal and that the cells in the heart muscle will make more effective use of some types of electrical energy and less effective use of other types of electrical energy. The prior art technique of using a minimum DFT energy of the defibrillation countershock to establish safety margins effectively ignores the accepted fact that defibrillation countershock waveforms which differ in shape, tilt and duration, for example, can have significantly different defibrillation threshold energies. In contrast, the effective current $I_{pe}$ as used by the present invention automatically compensates for any differences in the effectiveness of different waveforms. Consequently, the ICD of the present invention uses a minimum effective current $I_{pe}$ delivered to the heart muscle, rather than using a minimum DFT energy, as the measure for insuring an adequate safety margin for the device.

To understand how the present invention can use a minimum effective current $I_{pe}$ to insure an appropriate safety margin for the ICD, it is necessary to recognize that the objective of any defibrillation countershock is to generate an electric field across as much as possible of the heart muscle, the myocardium. This electric field must have a current strong enough to extinguish all cardiac depolarization wavefronts in the myocardium, and the current must be strong enough to prevent the myocardium cells from being restimulated during their vulnerable period. In essence, the present invention recognizes that the electric current generated by the defibrillation countershock must be larger than whatever minimum electric current is required for cell stimulation by at least a sufficiency ratio that will insure successful defibrillation. In this way, the use of an effective current $I_{pe}$ can be thought of as a correction factor applied to the actual current of the defibrillation countershock in order to compensate for the cellular phenomenon that currents below some minimum value simply do not have any effect on the cells.

It has long been known that in order to stimulate cells, a current applied to those cells must have a value at least equal to a rheobase value of those cells, otherwise the current applied to the cells is not effective in stimulating the cells. G. Wiess, "Sur la Possibilite de Rendre Comparable entre Eux les Appareils Suivant a l'Excitation Electrique", *Arch. Ital. deBiol.*, Vol. 35, p. 41 (1901); and L. Lapicque, "Definition Experimetelle de l'excitabilite", *Proc. Soc. deBiol.*, Vol. 77, p. 280 (1909). Lapicque defined the rheobase value as the stimulating current required for a pulse of infinite duration. From this definition, he further defined a chronaxie value ($d_c$) to be the duration of a pulse that required a current twice that of the rheobase value. These two works have been combined in the literature to define a strength-duration model for the required average current for neural stimulation known as the Weiss-Lapicque strength-duration curve, an example of which is shown in FIG. 12.

The present invention builds on the Weiss-Lapicque strength-duration model to define a physiologically effective current $I_{pe}$ as a simple model for the efficiency of a monophasic defibrillation countershock in terms of the actual average current of the defibrillation countershock. The actual average current ($I_{ave}$) is given by the amount of electrical charge delivered at the electrode leads divided by the duration of the pulse delivering that charge. The end result of the derivation of a definition of effective current $I_{pe}$ as taught by the present invention is that the effective current $I_{pe}$ is given by the charge delivered to the electrode leads divided by the sum of the pulse duration (d) and the chronaxie time constant for the heart ($d_c$). Expressing the charge delivered to the electrode leads in terms of the actual average current $I_{ave}$ yields a definition equation as follows:

$$I_{pe} = (I_{ave} * d)/(d + d_c) \quad \text{(Eq. 5)}$$

It can be seen from Eq. 5 that if the chronaxie value $d_c$ were zero, the effective current $I_{pe}$ would simply be $I_{ave}$, the average current of a monophasic defibrillation countershock. In this way, the definition of an effective current $I_{pe}$ distills the information contained in the Weiss-Lapicque strength duration curve to correct the actual average current $I_{ave}$ of a monophasic defibrillation countershock in order to compensate for the chronaxie phenomenon of the cells of the myocardium.

When a minimum effective current $I_{pe}$ is used to select and arrange the internal components of a capacitor-discharge ICD, the end result is a pair of surprising and non-intuitive conclusions.

First, the optimum capacitance value for the capacitor in a capacitor-discharge ICD is not determined by any stored or delivered energy requirement, but instead is a relatively constant value much smaller than any currently used capacitance values. The use of a minimum effective current $I_{pe}$ predicts that the optimum capacitance value will be a function of only the chronaxie time constant and the inter-electrode resistance of the electrode leads. This means that a capacitor with a smaller effective capacitance actually delivers a defibrillation countershock with more effective current $I_{pe}$ than a capacitor having a larger effective capacitance. When the optimum capacitance value is analyzed in terms of effective current $I_{pe}$, it is found that the optimal capacitance value is given by the formula:

$$C = (0.8 * d_c)/R \quad \text{(Eq. 6)}$$

Second, there is no single optimum pulse duration for a defibrillation countershock having an arbitrary capacitance value. Instead, a defibrillation countershock of a shorter duration can provide a more effective current $I_{pe}$ than a defibrillation countershock of a longer duration. The use of a minimum effective current $I_{pe}$ predicts that the optimum pulse duration is a compromise between the RC time constant of the capacitor-discharge circuitry and the heart's defibrillation chronaxie time constant, $d_c$. Thus, the predicted optimum pulse duration is not a constant, but rather is a function of the effective capacitance and other variables. The predicted optimum pulse duration can be most simply, and robustly, expressed as a fixed tilt or exponential decay followed by a fixed time duration extension. When the optimum pulse duration value is analyzed in terms of effective current $I_{pe}$, it is found that the optimal pulse duration is given by the formula:

$$d = ((R*C) + d_c)/(e - 1) \quad \text{(Eq. 7)}$$

Because the physical size of the capacitor is a function of its capacitance rating, the use of a capacitor with a smaller effective capacitance provides for a significant reduction in the displacement volume of the capacitor. In addition, because less energy is required to charge up a capacitor with a smaller effective capacitance, a battery with a smaller total energy storage, and, hence, a smaller displacement volume, may also be used. Finally, the shortening of the duration of the defibrillation countershock further decreases the energy requirements of both the capacitor and the battery, and also improves the safety margin of the device. In the preferred embodiment, several additional innovations are also used to further enhance the effectiveness of the defibrillation countershock and decrease the energy storage requirements of the ICD.

As a result of all of these improvements in the selection and arrangement of the internal components of the ICD of the present invention, the capacitor in the device only needs to store a maximum $E_c$ of less than about 30 Joules, and preferably less than 27 Joules. The effective capacitance of the capacitor required by the present invention can be less than 120 μF, and preferably less than about 95 μF. By optimizing both the charging time and the countershock duration for the smaller maximum $E_c$, the size of the battery required by the present invention is reduced because the total energy storage capacity of the device can be less than about 1.0 Amp-hours. In the preferred embodiment, the charging time for each defibrillation countershock is reduced to less than about 10 seconds and the pulse duration of a monophasic defibrillation countershock, or of a first phase of a multiphasic defibrillation countershock, is reduced to less than about 6 milliseconds.

By significantly reducing the displacement volume of both the capacitor and the battery, the overall displacement volume of an ICD in accordance with the present invention can be reduced below 90 cc, and preferably to between 40-60 cc. Because the size requirements for effective pectoral implantation will be distributed across the range from 40-90 cc for the entire population, it is obvious that the smaller the overall displacement of the ICD, the greater the percentage of human patients who can benefit from pectoral implantation of the device. At the displacement volumes provided for by the present invention, subcutaneous implantation of the device in the pectoral region of a human patient can be quite practical and effective.

Accordingly, it is a primary objective of the present invention to provide an implantable cardioverter defibrillator (ICD) having a smaller displacement volume than existing ICDs that permits effective subcutaneous implantation of the ICD in the pectoral region of human patients.

It is another primary objective of the present invention to provide an ICD that delivers a maximum defibrillation countershock optimized in terms of a minimum physiologically effective current ($I_{pe}$), rather than a minimum defibrillation threshold (DFT).

It is a further primary objective of the present invention to provide an ICD with a discharge-capacitor that stores a maximum electrical charge energy ($E_c$) of less than about 30 Joules.

It is a still further primary objective of the present invention to provide an ICD that utilizes a discharge-capacitor having an effective capacitance of less than 120 $\mu F$ to store the electrical charge for the cardioversion/defibrillation countershock.

It is another objective of the present invention to provide an ICD that delivers a monophasic defibrillation countershock, or a first phase of a multiphasic defibrillation countershock, having a pulse duration of less than about 6 milliseconds.

It is a further objective of the present invention to provide an ICD that has a battery and capacitor selected such that the battery can charge the capacitor to its maximum $E_c$ in less than about 10 seconds.

It is a still further objective of the present invention to provide an ICD with a five year life and a battery having a total storage capacity of less than about 1.0 Amp-hours.

These and other objectives of the present invention will become apparent with reference to the drawings, the detailed description of the preferred embodiment and the appended claims.

BRIEF DESCRIPTION OF THE DRAWINGS

FIGS. 6 and 7 are plan views, showing the interior of the preferred embodiment of the ICD of the present invention.

FIG. 8 is a voltage versus time graph showing the relative distribution of the defibrillation energy discharged from the capacitor of the preferred embodiment of the ICD of the present invention.

FIGS. 9 and 10 are voltage versus time graphs and a comparison table, respectively, showing the defibrillation energy discharged from the capacitor used in the preferred embodiment of the ICD of the present invention versus the defibrillation energy discharged from a capacitor in a prior art ICD.

FIG. 11 is a defibrillation success curve used to define a minimum. defibrillation threshold (DFT) for prior art ICDs for monophasic intravenous defibrillation countershocks.

DETAILED DESCRIPTION OF THE PREFERRED EMBODIMENT

In describing the present invention, first a description of the preferred mechanical arrangement of the internal components of the implantable cardioverter defibrillator (ICD) will be presented to provide a context for the remainder of the description. Next, a mathematical explanation of the derivation of the physiologically effective current ($I_{pe}$) as used by the present invention will be presented. Then, each of the major features responsible for decreasing the overall displacement volume of the ICD will be described. These features include: the use of a more optimal pulse duration and pulse waveform for the cardioversion/defibrillation countershock, the use of a capacitor having a smaller effective capacitance value, and the use of an improved battery configuration having a smaller total energy storage.

Mechanical Arrangement of the ICD Components

Figure 1:
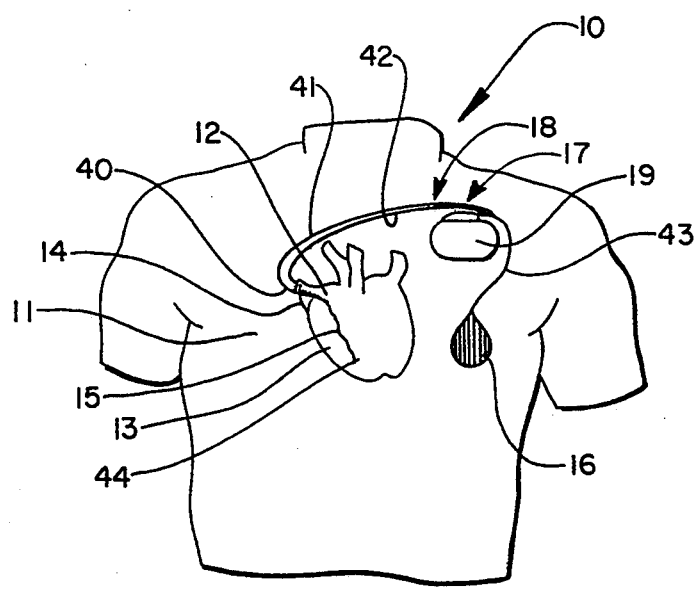
FIG. 1 is a frontal plan view showing the automatic, implantable cardioverter defibrillator of this invention implanted in the pectoral position of a human patient.

FIG. 1 shows an automatic ICD 17 of the present invention implanted in the pectoral region 18 of the chest 11 of patient 10. The ICD 17 has a plurality of connector ports for connection to various implantable catheter and other electrode means, as is known in the art. For example, electrode leads 41 and 42 are shown extending form the ICD 17 to catheter electrodes 40 and 15 which are passed, respectively, into the superior vena cava 14 and the right ventricle 13 of heart 12. Further, lead 43 is shown extending from the ICD 17 to a subcutaneous patch electrode 16. The specific configuration of the electrodes of the defibrillation system is dependent upon the requirements of the patient as determined by the physician.

Figure 3:
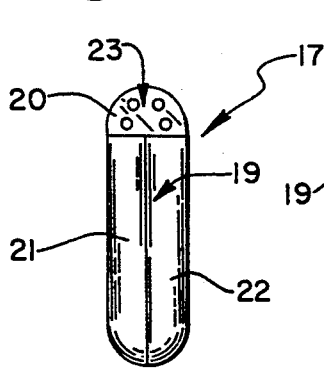
FIGS. 2 and 3 are frontal and side plan views, respectively, of the preferred embodiment of the ICD of the present invention.
Figure 2:
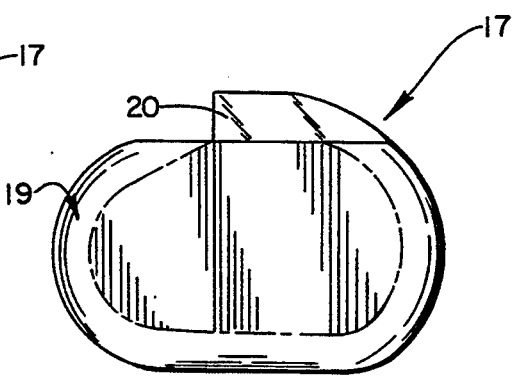

FIGS. 2 and 3 show the ICD 17 comprised of a housing 19 having mating half shells 21 and 22. Positioned and mounted on top of housing 19 is a top connector portion 20 having a plurality of connecting ports 23 which are described further below. Importantly, the ICD 17 is comprised of a compact, self contained structure having predetermined dimensions which permits pectoral implantation. The housing 19 and top connector 20 are constructed and arranged to yield a cooperating structure which houses power means, control means and capacitive means. This cooperating structure permits subcutaneous implantation in the pectoral region of a human patient and provides a compact and effective ICD that automatically senses the bioelectrical signals of the heart and is able to provide a 750 volt capacitive discharge, for example, to the heart for defibrillation purposes.

In the past, ICDs have required a size and configuration for functional purposes that necessitated implantation in the abdominal cavity of a patient. Such implantation has resulted in patient discomfort. However, the physical parameters of these prior art devices have prevented pectoral implantation, which is preferred by physicians and patients alike. Table 1 below shows the size and weight comparisons between known prior art ICD devices and the ICD 17 of the present invention.

TABLE 1

|  | Prior Art Device % of total (by volume) | Present Device % of total Device (by volume) | Present Device % of Prior Art Devices (by volume) | Present Device % of Prior Art Devices (by weight) |
|---|---|---|---|---|
| Connector | 10 | 8 | 30 | 32 |
| Capacitors | 30 | 38 | 63 | 62 |
| Batteries | 30 | 23 | 38 | 57 |
| Electronics | 30 | 31 | 50 | 40 |
| Total | 100% | 100% | 50% | 55% |
|  | (120 CC) | (60 CC) |  |  |

As shown in Table 1, the ICD 17 of this invention, provides a structure which is 50% of the volume of prior art devices and which has a weight which is 55% of the weight of the prior art devices. The connector port, capacitor, battery and electronic circuitry of the ICD 17 of the present invention are further described below.

It is important in this invention that the ICD 17 be constructed and arranged to minimize the overall displacement volume of the device to allow for pectoral implantation, for example. The housing structure 19 is a compact and lightweight structure made of a biocompatable material and has a contoured configuration. The overall structure of this invention has a weight of less than 130 grams, and preferably less than 120 grams, and a volume of less than 90 cc, and preferably between about 40–60 cc. As shown in Table 1, the ICD 17 of this invention has generally 55% of the weight of prior art devices and a volume which is generally 50% of that of prior art devices. Table 1 further shows the weights and volumes of the respective components of this invention (connector, capacitor, batteries and electronics) as a percentage in weight and volume of the total and in comparison to prior art devices.

As further shown in FIGS. 2 and 3, the housing structure 19 has a contoured periphery which is matingly connected to the top connector member 20 which also has a mating contoured configuration. The housing 19 is constructed of a biocompatable material such as a titanium or a stainless steel alloy. The top connector member 20 is also constructed of a biocompatable material, such as a biocompatable polymeric composition. It has further been found that for pectoral implantation purposes, the housing structure 19 have a desired length to width to thickness ratio of approximately 5 to 3 to 1.

When selected in accordance with the optimized minimum physiological current ($I_{pe}$) as described below, the capacitor has an effective capacitance of approximately 85 $\mu$F, is constructed and arranged to deliver an initial discharge voltage $V_d$ of 750 Volts, yielding the effective defibrillation countershock which is also described below. In the preferred embodiment, the effective discharge voltage and capacitance is achieved by using two flashtype capacitors in series, each having a capacitance rating of 170 $\mu$F and a voltage rating of 375 Volts, while occupying a total displacement volume of only 7 cc each. The output of the capacitors is in communication with an electronic circuitry output portion that generally is comprised of a flash type circuit which delivers the capacitor discharge through electrodes 15, 16 and 40, for example.

Figure 5:
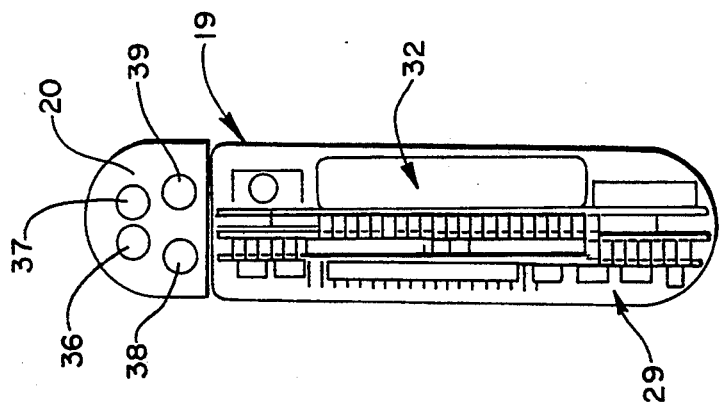
FIGS. 4 and 5 are side and frontal plan views, respectively, showing the power, capacitor, circuit and connector ports means positioned in the preferred embodiment of the ICD of the present invention.
Figure 4:
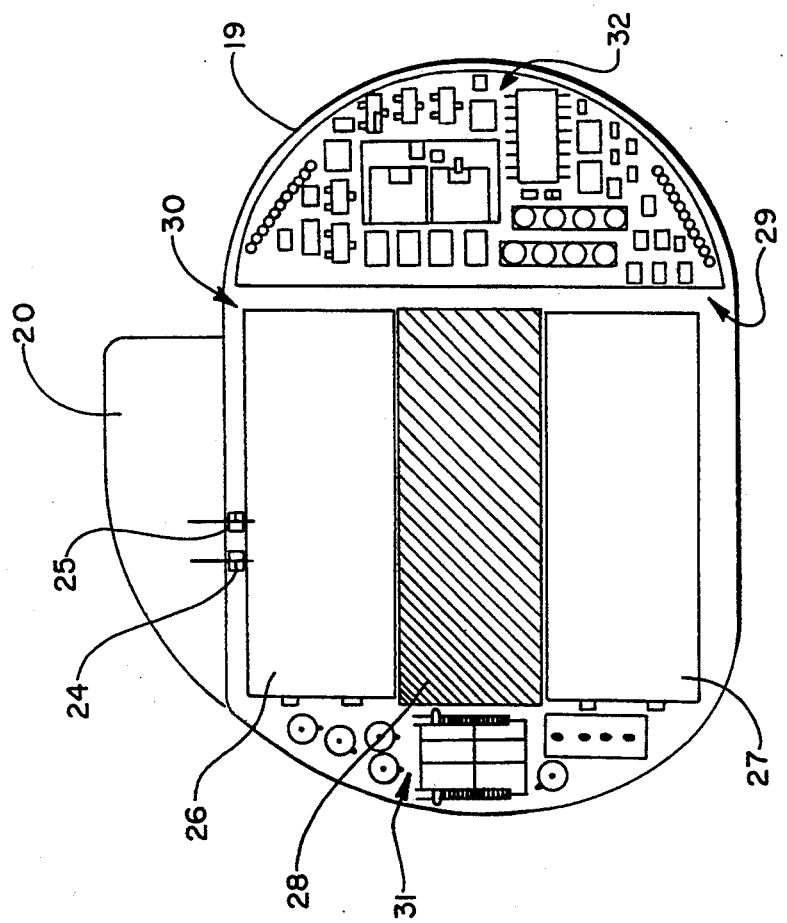

FIGS. 4 and 5 show the canister housing 19 having an interior space 30 wherein capacitors 26 and 27 are positioned and wherein a battery system 28 and circuit board portions 31 and 32 are positioned. The top connector 20 is shown mounted to the top of the canister housing 19. Connecting ports 36, 37, 38 and 39 are shown positioned in the top connector 20. The connector ports 36 and 37 are connectible to the positive defibrillating electrode, for example, while connecting port 38 is connectible to the negative defibrillating electrode, for example, and the connecting port 39 receives the pacing/sensing electrode leads 41, 42. Channels 24 and 25 provide communicative and fastener members that provide for the attachment of the top connector 20 to the canister housing 19 and for the electrical connection between the ports 36, 37, 38 and 39 and the electronic elements positioned in the interior space 30 of housing 19.

As discussed, the top connector 20 of the defibrillator ICD 17 has, for example, connecting ports 36 (DF+), 37(DF+), 38(DF−) and 39 (sensing/pacing). The lead connected to the DF− port, for example, is in conductive contact with the catheter electrode 15 placed in the right ventricle 13 of the heart 12. The electrode lead(s) connected to the DF+ port(s) are connected to either or both of the electrodes positioned in the superior vena cava 14 and the subcutaneous patch electrode 16. Alternatively, the DF+port holes may not be utilized, and plugged by a stopper means, for example, when the ICD body itself is utilized as the positive element to complete the defibrillation circuit. The pacing/sensing electrode 44 provides an input to connecting port 39 of the ICD 17 and provides continual monitoring of cardiac signals from the heart. The circuitry of the ICD 17 has means to detect any tachycardiac or other arrhythmia condition and to thereby respond by the selective discharge of electrical energy stored in the capacitors 26 and 27.

As described in more detail below, the ICD 17 of this invention provides a device which utilizes smaller capacitors and batteries than those of prior art devices and thus yields a countershock generator device having a smaller displacement volume that permits effective implantation of the device in the pectoral region of a human patient. Although the smaller unit and associated components are smaller and deliver a smaller energy countershock to the heart, the implantation of the device in the pectoral region provides for a better countershock vector. Together with the improved countershock pulse waveform as described below, the ICD 17 produces a more effective defibrillation/cardioversion countershock than prior art ICD devices.

FIGS. 6 and 7 show the mating housing half shells 21 and 22, respectively of canister housing 19. The half shell 22 is shown to have an interior peripheral band 34 which is fixed adjacent the peripheral edge 33. The interior peripheral band 34 extends outwardly from the edge 33 of half shell 22 and is constructed and arranged to receive the peripheral edge 35 of housing half shell 21. Alternatively, the peripheral band 34 may be mounted within housing half shell 21, whereby the half shell 22 is positioned thereabout. The peripheral band 34 is also provided to shield the electronic components within housing 19 during the welding process uniting the body shells 21 and 22.

The flexible circuit board 29 is mounted within the interior space 30 of housing 19. The circuit board 29 provides for the sensing/pacing circuitry in communication with the lead extending from connecting port 39, for example. When a fibrillation episode is detected, the circuit board 29 causes the capacitors 26, 27 to discharge an initial 750 Volt charge through the electrode leads connected to ports 36-38, for example, and to the heart 12 of the patient 10. The electronic circuitry has a sensing portion which monitors the heart beat rate irregularity by means of two small electrodes 44, as is known in the art. In the preferred embodiment, the circuitry further has a processor portion which determines, with respect to a predetermined standard, when the output portion of the circuit will be activated.

FIG. 8 is a graph showing the voltage discharge with respect to time from the 140 μF capacitor used in an existing ICD. The graph shows the incremental benefit of the voltage discharge with respect to time. As shown no benefit is achieved after 6-7 ms of countershock delivery. FIG. 9 is a graph which shows the instantaneous voltage with respect to time and compares the plotted values of a countershock having the same delivered energy content for both the present invention and a typical prior art ICD. In FIG. 9, the countershock is a 20 Joule delivered energy monophasic countershock and it will be seen that the pulse duration of the countershock in accordance with the present invention is significantly shorter than the pulse duration of the countershock delivered by the prior art ICD.

As summarized in the table of FIG. 10, the 85 uF capacitor of the preferred embodiment of the present invention provides 25.33 Joules of delivered energy in the form of a biphasic defibrillation countershock having a delivery efficiency of 97.5% from a 26 Joule maximum $E_c$ stored in the capacitors 26, 27. In comparison, the 140 μF capacitor used in a prior art ICD device provides 34 Joules of delivered energy in the form of a monophasic defibrillation having a delivery efficiency of 86.3% from a maximum $E_c$ stored in the capacitor of 39.4 Joules. The effective current $I_{pe}$ of the biphasic countershock delivered by the present invention is 5.67 Amps, uncorrected, and possibly as high as 6.55 to 7.32 Amps, when corrected to be a monophasic equivalent current. In contrast, the effective current $I_{pe}$ of the monophasic countershock delivered by the prior art device is 6.79 Amps. Thus, the uncorrected $I_{pe}$ of the present invention is only 20% less than the $I_{pe}$ of the prior art device, while the maximum $E_c$ of the present invention is more than 50% less than the maximum $E_c$ of the prior art device.

When the corrected $I_{pe}$ provided by the biphasic countershock of the preferred embodiment of the present invention is compared, the present invention provides essentially the same effective current $I_{pe}$ as the prior art device with half the maximum $E_c$ and, as little as half the requisite displacement volume for the capacitor. Depending upon the correction factor applied to convert the current efficiency of an optimized biphasic countershock pulse to a traditional monophasic countershock pulse (a 25% more energy efficient countershock is a 15% more efficient effective current, whereas a 40% more energy efficient countershock is a 28% more efficient effective current), the corrected $I_{pe}$ of the present invention is between 3% less to 7% more than the $I_{pe}$ of the prior art device.

Derivation of the Physiologically Effective Current ($I_{pe}$)

The famous Weiss-Lapicque model was developed at the turn of the century. It was an empirical model and the first physiological explanation for why the model accurately predicts the required current for cellular stimulation was only recently explained. Irnich, W., "The Fundamental Law of Electrostimulation and its application to Defibrillation", PACE 1990, 13 (Part 1): 1433-1447. The model gives the required (average) current for neural stimulation as:

$$I_{ave} = K_1 + (K_2/d) \qquad \text{(Eq. 8)}$$

with d being the pulse duration. The value K1 is the current required for an infinite duration pulse. The "chronaxie" is that duration which requires a doubling of the rheobase current. The chronaxie time constant $d_c$ is thus given by:

$$d_c = K_2/K_1 \qquad \text{(Eq. 9)}$$

Defining $I_r$ as the rheobase current gives:

$$I_{ave} = I_r * [1 + (d_c/d)] \quad \text{(Eq. 10)}$$

Figure 12:
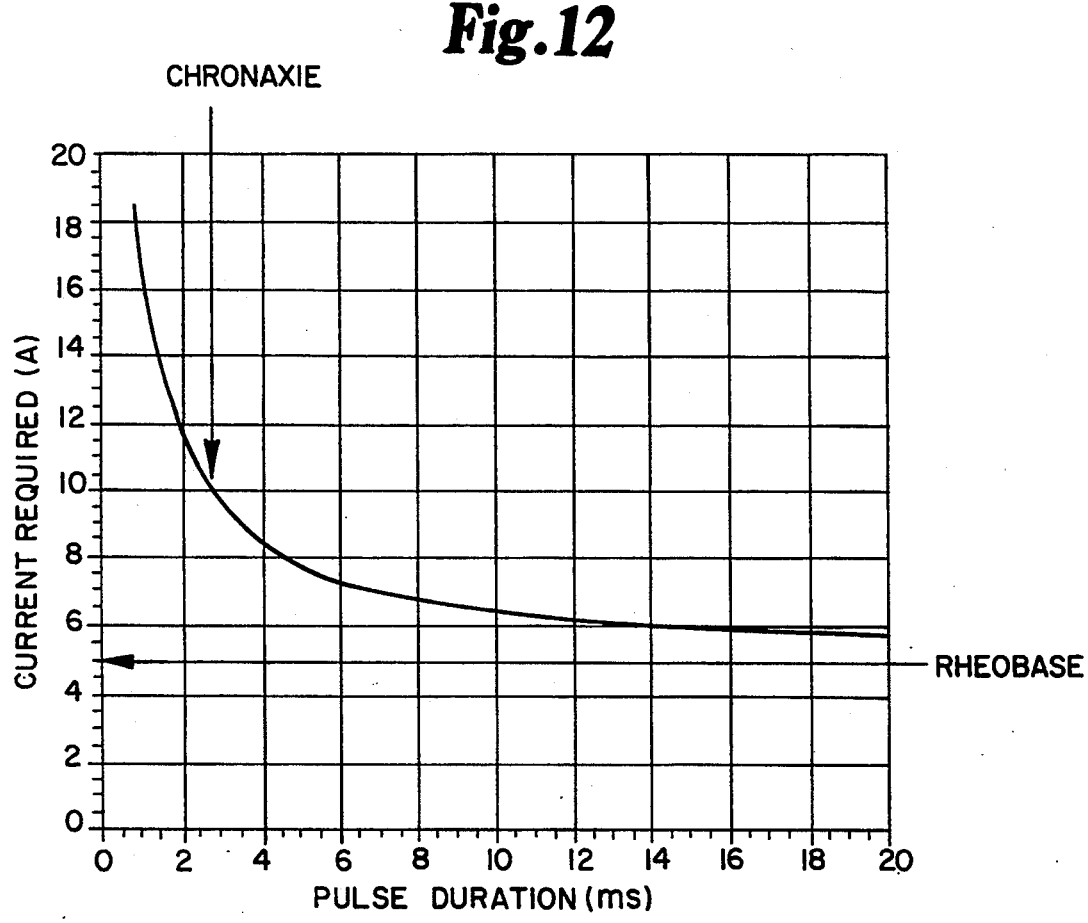
FIG. 12 is a typical Weiss-Lapicque strength-duration curve showing the average current required for defibrillation as a function of the pulse duration.

The Weiss-Lapicque model was based on cell stimulation, not defibrillation. However, in 1978, Bourland et al showed, with a study of dogs and ponies, that defibrillation thresholds also followed the Weiss-Lapicque model when current averaged over pulse duration was used. Bourland, J. D., Tacker, W. A. and Geddes, L. A., "Strength Duration Curves for Trapezoidal Waveforms of Various Tilts for Transchest Defibrillation in Animals", *Med. Instr.*, (1978), Vol. 12, No. 1:38–41. A typical strength-duration curve is shown in FIG. 12.

Bourland et al. further proposed that the average current of a pulse was the best measure of its effectiveness when compared to other pulses of the same duration. This was found to hold fairly true for pulses from 2–20 ms in duration, regardless of waveform. Bourland, J. D., Tacker, W. A. and Geddes, L. A., et al. "Comparative Efficacy of Damped Sine Wave and Square Wave Current for Transchest Ventricular Defibrillation in Animals", *Med. Instr.*, (1978), Vol. 12, No. 1:42–45.

Numerous studies have confirmed the strength-duration relationship for defibrillation currents. These same studies show that the defibrillation chronaxie time constant, $d_c$, is in the range of 2–4 ms. Using the available data on measured defibrillation chronaxie time constants, $d_c = 2.7 \pm 0.9$ ms is the average chronaxie value for the human heart.

In contrast to the accepted prior art technique of using a minimum defibrillation threshold energy (DFT) to measure the effectiveness of a defibrillation countershock, or even in contrast to the suggestion by Bourland et al to use the average current, the present invention defines an effective current as that percentage of the rheobase requirement for the human heart that the average current of a defibrillation countershock pulse can satisfy. Under this definition, successful defibrillation will require that $$I_{ave} \geq I_4 * [1 + (d_c/d)] \quad \text{(Eq. 11)}$$

where $I_{ave}$ is the current averaged over the pulse duration of the defibrillation countershock. Satisfying this condition and substituting $I_{pe}$ for $I_r$ yields a definition of physiologically effective current ($I_{pe}$) which can be expressed in several ways:

$$I_{pe} = I_{ave}/[1 + (d_c/d)] \quad \text{(Eq. 12)}$$
$$= (I_{ave} * d)/(d_c + d) \quad \text{(Eq. 13)}$$
$$= \text{delivered charge}/(d_c + d) \quad \text{(Eq. 14)}$$

Note that the effective current of a defibrillation countershock only equals the rheobase current when the output of the pulse is exactly operated at the defibrillation threshold, and, hence, with a zero safety margin. In general, the two parameters are not equal in value or orientation. The effective current $I_{pe}$ is a system variable of the ICD, while the rheobase current $I_r$ is primarily a physiologic variable.

Figure 13:
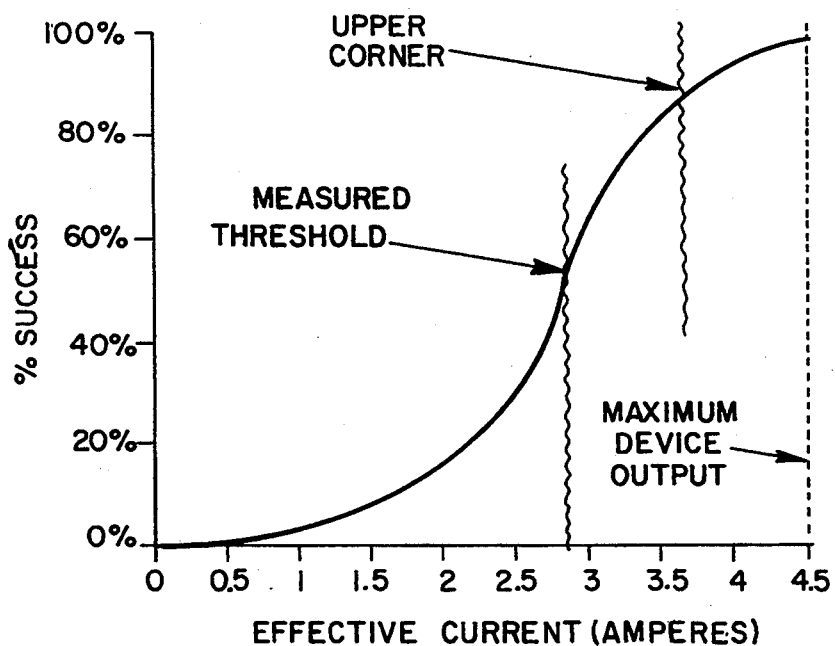
FIG. 13 is a defibrillation success curve for the present invention using an physiologically effective current ($I_{pe}$) for monophasic intravenous defibrillation countershocks.
Figure 14:
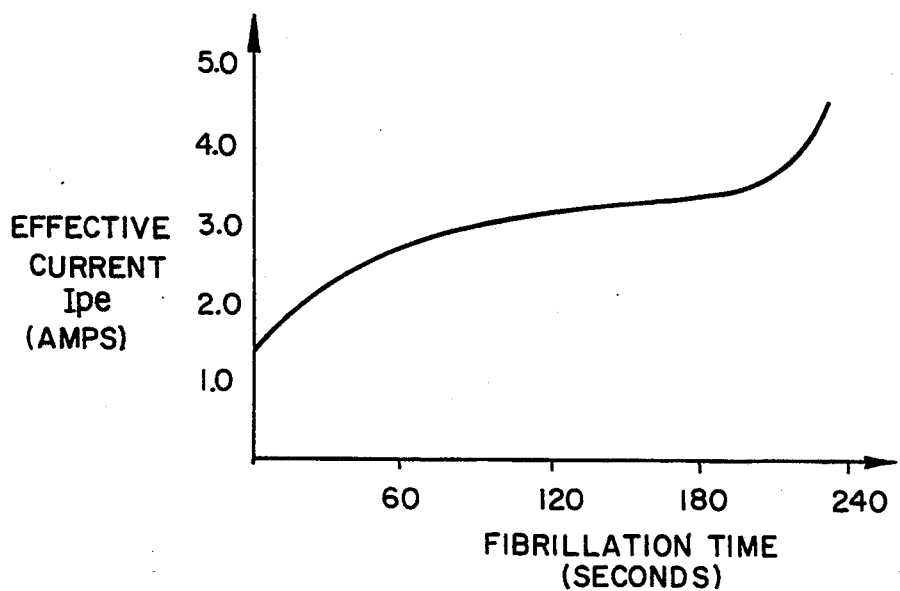
FIG. 14 is a graph of the minimum effective current ($I_{pe}$) for monophasic intravenous defibrillation countershocks versus fibrillation time showing the impact of prolonged fibrillation on minimum $I_{pe}$.

FIG. 13 shows a defibrillation success curve for monophasic intravenous defibrillation countershocks plotted in terms of the effective current $I_{pe}$ of the present invention. It will be apparent when comparing the $I_{pe}$ defibrillation success curve shown in FIG. 13 with the DFT defibrillation success curve shown in FIG. 11 that the $I_{pe}$ curve is tighter and the necessary safety margin is much closer to the median $I_{pe}$ required for effective defibrillation. FIG. 14 is a graph of the minimum $I_{pe}$ for monophasic intravenous defibrillation countershocks versus fibrillation time showing the impact of prolonged fibrillation on minimum $I_{pe}$. Together, these figures illustrate how a device with a smaller maximum $E_c$ can still provide a more than adequate safety margin, as long as the effective current $I_{pe}$ of the defibrillation countershock is sufficient. The next two sections of the description set forth how to optimize the characteristics of a cardioversion/defibrillation countershock in terms of effective current $I_{pe}$.

Optimal Pulse Waveform and Duration

The present invention uses the effective current $I_{pe}$ model to find the optimum pulse duration for a conventional, time-truncated, capacitor discharge defibrillation countershock waveform. In such a capacitor-discharge system, a capacitance (C) is charged to an initial voltage ($V_i$) and then discharged into the effective load resistance (R) of the heart for a pulse duration (d), at which time the capacitance will have a final voltage (V f). The amount of droop in the capacitor-discharge waveform at the time the pulse is truncated has been referred to as the "tilt" of the waveform as given by the equation:

$$\text{tilt} = (V_i - V_f)/V_i \quad \text{(Eq. 15)}$$
$$= 1 - V_f/V_i$$

Substituting the RC time constant exponential decay for $V_f/V_i$ yields:

$$\text{tilt} = 1 - e^{-d/RC} \quad \text{(Eq. 16)}$$

where RC is the capacitor-discharge system time constant, also known as $\tau$. Substituting the system parameters for C, V and tilt for the delivered charge in Eq. 14, the effective current $I_{pe}$ can also be expressed as:

$$I_{pe} = (C * V * \text{tilt})/(d_c + d) \quad \text{(Eq. 17)}$$
$$= (C * V * (1 - e^{-d/\tau}))/(d_c + d)$$

Because the first derivative of $I_{pe}$ approaches zero at extreme values of d, its maximum is at the point of zero derivative.

$$0 = \partial I_{pe}/\partial d \quad \text{(Eq. 18)}$$
$$= CV_i[[(d_c + d)[1/\tau e^{-d/\tau}] - [1 - e^{-d/\tau}]]/(d_c + d)^2]$$
$$= [(d + d_c)/\tau]e^{-d/\tau} - 1 + e^{-d/\tau}$$
$$= [[(d + d_c)/\tau] + 1]e^{-d/\tau} - 1$$

Normalizing Eq. 18 to the system time constant by defining:

$$z = d/\tau \quad \text{(Eq. 19)}$$
$$a = d_c/\tau \quad \text{(Eq. 20)}$$

The derivative of Eq. 18 now reduces to $$0 = (z + a + 1)e^z - 1 \quad \text{(Eq. 21)}$$

Multiplying by $-t^z$ and defining f(z) gives:

$$0 = e^z - a - a - 1 \equiv bf(z) \quad \text{(Eq. 22)}$$

This transcendental equation cannot be solved in closed form, so the Newton-Raphson approximation is used. If $z_0$ is the first approximation for the root, then $z' = z_0 - (f(z_0)/f'(z_0))$ is the Newton-Raphson approximation for Eq. 22. Present ICD devices favor a tilt of about 65%. This implies that the countershock pulse duration is roughly equal to one system time constant ($d \approx \tau$). Because $z = d/\tau \approx 1$, the first approximation is $z_0 = 1$. Thus:

$$z' = z_0 - (f(z_0)/f'(z_0)) \quad \text{(Eq. 23)}$$
$$= 1 - [(e - 1 - 1 - a)/(e - 1)]$$
$$= (1 + a)/(e - 1) \quad \text{(Eq. 24)}$$

Denormalizing Eq. 24 gives:

$$d \approx \tau[(1+(d_c/\tau)/(e-1)] \quad \text{(Eq. 25)}$$

This gives the expression for optimal pulse duration of a time truncated monophasic capacitor discharge:

$$d = (\tau + d_c)/(e-1) \quad \text{(Eq. 26)}$$

Numerical optimization shows that this estimate gives an $I_{pe}$ within 0.2% of true optimum for typical values of R, C and de. For extreme values the maximum error in the resulting $I_{pe}$ is less than 2.0%. It should also be noted that $(e-1) = 1.72 \approx 2$. Thus, the optimal pulse duration, d, is approximately equal to the average of the capacitor time constant and the heart's chronaxie time constant. In other words, the model suggests that the best pulse duration is a compromise between the time required to deliver the capacitor's charge, $\tau = RC$, and the time required to match the timing of the heart, $d_c$.

The predicted optimum d may be used to directly derive the optimum tilt for the countershock pulse from Eqs. 16 and 26.

$$\text{tilt}_{opt} = 1 - e^{-d_{opt}/\tau} \quad \text{(Eq. 27)}$$
$$= 1 - \exp[-[(1 + (d_c/\tau))/(e - 1)]]$$

where, again, $\tau = RC$. Assume, for a moment, that RC is chosen to equal $d_c$. From Eq. 27 we have that $\text{tilt}_{opt} = 68.8\%$.

It will be noted that the predicted optimum tilt is rather high for small capacitance values. An intuitive explanation is that they need to spread their charge delivery over as great a duration as possible to come closer to the chronaxie time. Because the rheobase is small compared to the peak current, this lowering of average current is well tolerated. Conversely, for large capacitances the optimum tilt is smaller as the average current must remain above the rheobase.

The prediction by this model that small capacitor systems benefit from higher tilts is supported, but not predicted, by a prior study of truncated waveforms. Schuder, J. C. et al. "Transthoracic Ventricular Defibrillation in the Dog with Truncated and Untruncated Exponential Stimuli", *IEEE Trans. Bio. Eng.*, (1971); BME-18:410-415. This study showed that the greatest improvements from truncation are obtained with pulses with d>5 ms. In other words, high tilts are better tolerated with smaller pulse durations (which are generated by smaller capacitors).

Figure 15:
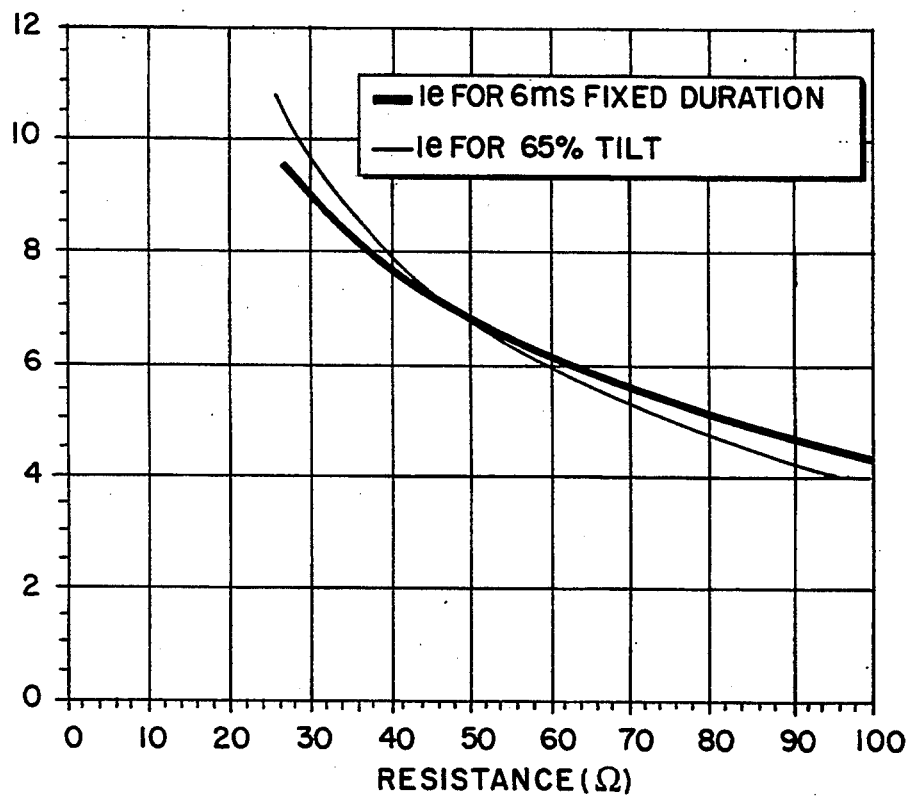
FIG. 15 is a graph of the minimum effective current ($I_{pe}$) for monophasic intravenous defibrillation countershocks as a function of electrode resistance for both fixed duration and tilt countershock pulses.

It will be understood that the inter-electrode resistance varies with the patient and positioning of the electrode leads and may change after implantation of the ICD. It is desirable that the pulse duration d remain close to optimum in spite of this change. FIG. 15 gives the effective current $I_{pe}$ for various inter-electrode resistances when the tilt and duration of the pulse were optimized for an assumed 50 $\Omega$ load. In this example, a 140 $\mu$F capacitor and a 2.7 ms chronaxie are assumed. One curve shows how the effective current $I_{pe}$ varies when tilt is used as the specification for the pulse duration, while the other reflects the use of a fixed time duration. Note that tilt best tolerates decreases in resistance while a fixed duration best handles increases in resistances.

The optimum pulse duration from Eq. 26 may be rewritten as:

$$d = 0.58 \, RC + 0.57 \, d_c \quad \text{(Eq. 28)}$$

Because $1 - e^{-0.58} = 44\%$, a pulse duration of 0.58 RC may be redefined as a 44% tilt. Thus, the optimum duration from Eq. 28 may be stated in words as:

1. Allow the capacitor voltage to decay by 44%, then
2. Continue the pulse for an additional 58% of the chronaxie time constant.

If we assume $d_c = 2.7$ ms, then this gives a 44% tilt followed by a 1.6 ms extension for optimum pulse duration. Note that this specification of the optimum pulse duration automatically adjusts the duration for any changes in resistance so that continued monitoring of the effective inter-electrode resistance is not required. In addition, using this specification of the optimum pulse duration gives an $I_{pe}$ in excess of that specified by either a fixed tilt or a fixed duration alone, for any resistance value.

The choice of a tilt or duration specification has been an open issue in defibrillation. Based on the predictions using the effective current model of the present invention, it would appear that the best choice is actually a composite of tilt and duration as given in Eq. 28. This specification for pulse duration is intuitively attractive in that it directly recites the necessary compromise between the electronics (duration sufficient for charge delivery) and the heart (duration close to chronaxie for efficiency).

The optimized pulse duration utilized by this invention can be applied to monophasic waveforms, or the first phase of a biphasic or multiphasic waveform. In the latter cases, when it is applied to the first phase of a waveform, subsequent phases of the waveform can be specified to have equal or lesser duration than the first phase. In the preferred embodiment, a biphasic waveform is used in order to take advantage of the additional decrease in the minimum effective current $I_{pe}$ required for effective defibrillation that is predicted by known clinical data showing a 25-40% decrease in minimum DFT energy thresholds for biphasic countershock pulses.

It will also be appreciated that the optimum pulse waveform and duration predicted by the use of the present model of effective current $I_{pe}$ are equally applicable to both cardioversion and defibrillation countershocks. Typically, cardioversion countershocks are countershocks that have total pulse energies of between 0.5 and 5 Joules, whereas defibrillation countershocks are countershock that have total pulse energies of greater than about 3 Joules. In each case, the present invention utilizes cardioversion/defibrillation countershocks which have pulse durations and waveforms optimized in terms of effective current $I_{pe}$ to produce a smaller total energy required for an effective countershock pulse.

Smaller Effective Capacitance Value

For a given capacitor technology, capacitor volume is proportional to the stored energy. To maximize the performance of an ICD, for a given displacement volume, one must therefore optimize the effective current $I_{pe}$ for a given maximum $E_c$ as defined by Eq. 1. Reworking Eq. 1 in terms of $V_d$:

$$V_d = ((2*E_c)/C)^{0.5} \tag{Eq. 29}$$

Combining Eq. 29 with the effective current $I_{pe}$ formula of Eq. 17 yields:

$$\begin{aligned}I_{pe} &= (C*V*\text{tilt})/(d_c + d) \\ &= (C*((2*E_c)/C)^{0.5}*\text{tilt})/(d_c + d) \\ &= ((2*E_c)^{0.5}*C^{0.5}*\text{tilt})/(d_c + d)\end{aligned} \tag{Eq. 30}$$

Substituting Eq. 26 for d and Eq. 27 for the optimum tilt gives:

$$\begin{aligned}I_e &= \frac{\sqrt{2E}\sqrt{C}\left\{1 - \exp\left[\frac{1 + d_c/RC}{1 - e}\right]\right\}}{\frac{RC + d_c}{e - 1} + d_c} \\ &= \sqrt{2E}\frac{\sqrt{C}\left\{1 - \exp\left[\frac{1 + d_c/RC}{1 - e}\right]\right\}}{\frac{RC + d_c}{e - 1} + d_c}\end{aligned} \tag{Eq. 31}$$

Note that the term for energy can be separated from the remainder of the expression. Thus, the optimum capacitance value is independent of the stored energy in the capacitor. The numerical solution is:

$$(R*C)/d_c = 0.795906 \approx 0.8 \tag{Eq. 32}$$

The solution is a reasonable result that implies that an RC time constant of the countershock pulse should be close to the "time constant" of the myocardial cells (i.e., the chronaxie value time constant) for optimum performance of the cardioversion/defibrillation countershock. This solution is accurate to 1% over a broad range of the exogenous variable R and $d_c$. The solution also suggests that there is no first order relationship between energy storage and optimum capacitance. In other word, to change the energy of an ICD, the effective current model of the present invention suggests that the voltage should be adjusted up or down, and that the capacitance should not be moved significantly from the ideal value.

Assuming a chronaxie of 2.7 ms and an inter-electrode resistance of 50 Ω, the optimum capacitance value from Eq. 32 is 43 μF. Using this capacitance value in Eq. 26 yields a pulse duration of 2.83 ms. This corresponds to a tilt value of approximately 73% (see Eq. 27). It will be noted that the 2.83 ms optimal duration is very close to the 2.7 ms assumed chronaxie time. Thus, the optimal pulse duration for the practical capacitive discharge pulse is close to that of an ideal rectangular pulse as represented by the chronaxie time constant, assuming that the capacitance value is optimized to about 43 μF.

As shown in FIG. 10, a presently approved ICD delivers a maximum defibrillation countershock monophasic pulse with an effective current $I_{pe}$ of 6.79 Amps from a 140 μF capacitor charged to 750 Volts. This requires a minimum $E_c$ of at least 39.4 Joules and a corresponding requisite volume for this storage. If the optimum capacitor value of 43 μF and a tilt of 73% were used, the same 6.79 Amps effective current $I_{pe}$ could be delivered from a charge of 1195 Volts that would involve an energy storage of only 30.7 Joules. In other words, the less efficient design of current ICDs with overly large capacitors requires 28% more energy requires 28% more capacitor volume for the device to deliver a monophasic countershock. As previously described, the battery volume in existing devices is necessarily larger to supply this increased minimum $E_c$.

As indicated in the background art section, when designed with present day microelectronic switches, such as power FETs, the optimal discharge voltage Vd of almost 1200 Volts is problematical. Thus, in the preferred embodiment a compromise in capacitor size is necessary. As a result, the optimum capacitance value selected for a discharge voltage $V_d$ of 750 Volts, is approximately 85 μF. As a result, the effective current $I_{pe}$ delivered by the preferred embodiment is 5.67 Amps. When the 13-29% increased efficiency of the effective current of a biphasic waveform is factored in, the present invention provides a monophasic equivalent effective current of between 6.55 to 7.32 Amps. Thus, the preferred embodiment that stores a maximum $E_c$ of about 26 Joules can actually be more effective than the prior art monophasic defibrillation countershocks that required a maximum $E_c$ of 39.4 Joules, yet only produces an effective current $I_{pe}$ of 6.79 Amps. In addition, this compromise on capacitor size of the preferred embodiment permits a simple implementation of the capacitor-discharge ICD, while obtaining the majority of the benefits of the reduced size of the capacitor, and, the corollary reduction in the size of the battery.

Improved Battery Configuration

For the battery, the physical size of the battery will be primarily a function of the amp-hours of storage capacity provided by the battery. In addition to the required maximum $E_c$, two other energy parameters are required in order to budget the storage capacity of a battery for an ICD. These parameters are the minimum number of countershocks that are to be delivered over the life of the device ($N_p$) and the idle current drain of the device when it is sensing the cardiac signals ($I_i$). Current ICDs budget for at least 200 defibrillation countershocks over the life of the device and idle currents are on the order of 15-20 μAmps.

Some ICDs also provide for pacing capabilities, in which case the required pacing energy must also be factored into the storage capacity of the battery. The current draw on a battery due to constant pacing can be estimated by assuming that the pacing countershock will have a 6 Volt amplitude, a 500 μsec width, and a 500 Ω assumed impedance, and that pacing will occur at a rate of 70 beats/minute. Under these conditions, the energy drawn from the battery will be about 2.5 mJoules/minute, or an average current draw of about 7 μAmps. It should be noted that the electrical energy necessary to provide for pacing capabilities is much less than even the idle current drawn by the ICD.

If an ICD is designed against an optimum battery budget that would support a device life (l) of five years, the total storage capacity ($E_t$) required for the battery is the sum of the maximum electrical charge energies, the maximum idle current energies and the maximum pacing energies. For existing ICDs, such a battery budget can be calculated as follows:

$$E_t = ((I_b * t_c) * N_p) + (I_i * I) + (I_p * I) \quad \text{(Eq. 33)}$$
$$= ((12 \text{ Amp-sec}) * 200) + (20 \mu A * 5 \text{ years}) + (7 \mu A * 5 \text{ years})$$
$$= (0.7 \text{ Amp-hours}) + (0.9 \text{ Amp-hours}) + (0.3 \text{ Amp-hours})$$
$$= 2.0 \text{ Amp-hours}$$

Most ICDs use a pair of 3 Volt, 2 Amp-hour lithium/silver vanadium oxide batteries to provide this amount of total storage capacity for the ICD. The lithium/silver vanadium oxide batteries represent the densest power source technology currently viable for use in an ICD. While improvements in battery technology may increase the storage density slightly, and thereby decrease the total volume of the power source somewhat, the total volume required by the power source for current ICDs must be sufficiently large to supply a total storage capacity ($E_t$) for the device of about 2.0 Amp-hours.

In contrast to the prior art, the present invention budgets a total storage capacity $E_t$ for the device of about 1.0 Amp-hours. This significantly smaller storage capacity $E_t$ is achieved primarily due to the smaller maximum $E_c$ for the device. Additionally, several innovations in capacitor charging and battery configuration of an improved battery system are utilized in the preferred embodiment to further reduce both the storage capacity $E_t$ and the overall displacement volume of the battery system. These innovations include: (1) the use of a dual battery configuration, one battery for the monitoring requirements and a different battery for charging the capacitor; (2) the use of a staged energy circuit with a rechargeable battery to charge the capacitor; and (3) the use of an intensifying battery to improve the energy delivery capability and decrease the current delivery requirements of the battery system when delivering multiple closely spaced defibrillation countershocks, such as during a fibrillation incident where the first cardioversion/defibrillation countershock is not successful.

Dual Battery Configuration

Current ICDs utilize a single battery system to provide all of the energy storage requirements for the device. Unfortunately, the ideal voltage requirements for the monitoring and capacitor-discharge functions of an ICD are almost opposites. For the monitoring function, it is desirable to use the lowest possible voltage that the circuits can operate reliably with in order to conserve energy. This is typically on the order of 1.5 to 3.0 Volts. On the other hand, the output circuit works most efficiently with the highest possible voltages, including up to 800 Volts. The single battery system of current ICDs is typically comprised of two lithium vanadium pentoxide cells in series that produce about have a battery output voltage ($V_b$) of about 6 Volts. This voltage $V_b$ is not ideal for either the monitoring or capacitor-discharge functions.

In the preferred embodiment of the present invention, two separate battery systems are used to provide the energy storage requirements of the ICD, one having optimized characteristics for the monitoring functions and one having optimized characteristics for the capacitor-discharge functions. The preferred battery system is a conventional pacemaker power source for the monitoring functions, such as a lithium iodide battery, that is optimized for long life at low current levels. The preferred battery system for the capacitor-discharge function is a conventional ICD battery, such as a lithium vandium pentoxide battery, that is optimized for high current drain capability and low self-discharge for long storage life with few discharges. Due to an excess of low current level in the conventional ICD battery used for the capacitor-discharge function, this battery can also power any pacing functions of the device without affecting its operational requirements to perform the capacitor charging function. By optimizing the two separate battery systems, the overall charge density of each battery can be increased and, hence, the combined volume of both battery systems can be decreased when compared to the single battery system found in the prior art.

Figure 16:
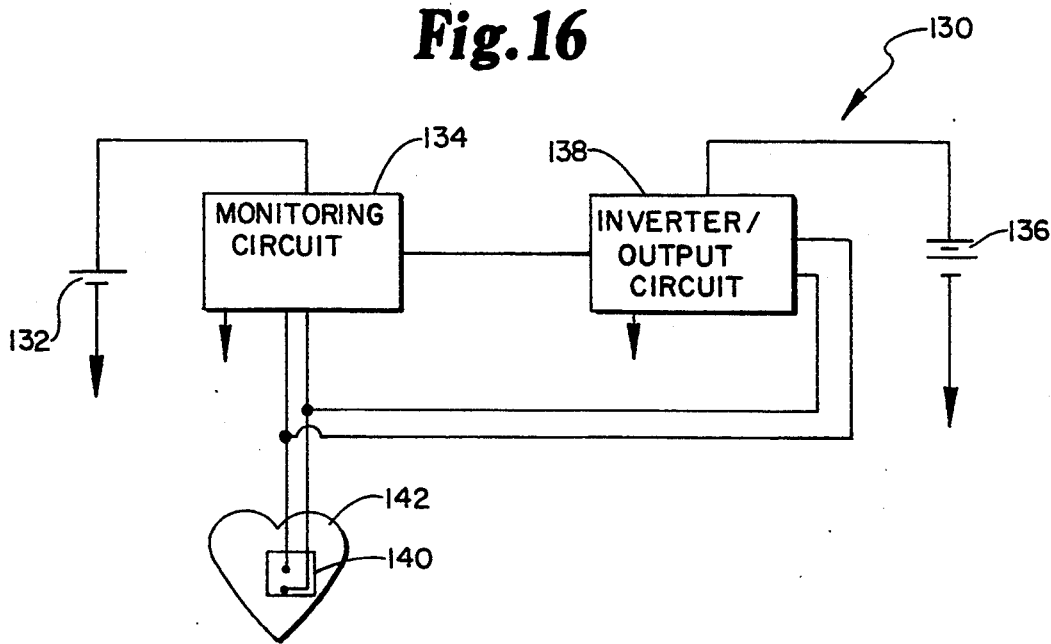
FIG. 16 is a block diagram of a dual battery system energy storage system for the preferred embodiment of the present invention.

FIG. 16 illustrates a block diagram of the preferred embodiment of the dual battery system 130. A battery 132 of appropriate voltage and minimum physical size connects to and powers a monitoring circuit 134 only. Another battery 136 of appropriate voltage and minimum physical size connects to and powers the capacitor-discharge output circuit 138 only. The monitoring circuit 134 and the capacitor-discharge output circuit 138 each connect to electrodes 140 positioned near or in the heart 142. The monitoring circuit 134 also connects to and triggers the capacitor-discharge output circuit 138 in the event an arrhythmia is detected. The battery systems 132 and 136 are optimally size electrically and physically to provide for the most efficient operation in the smallest displacement volume.

Figure 17:
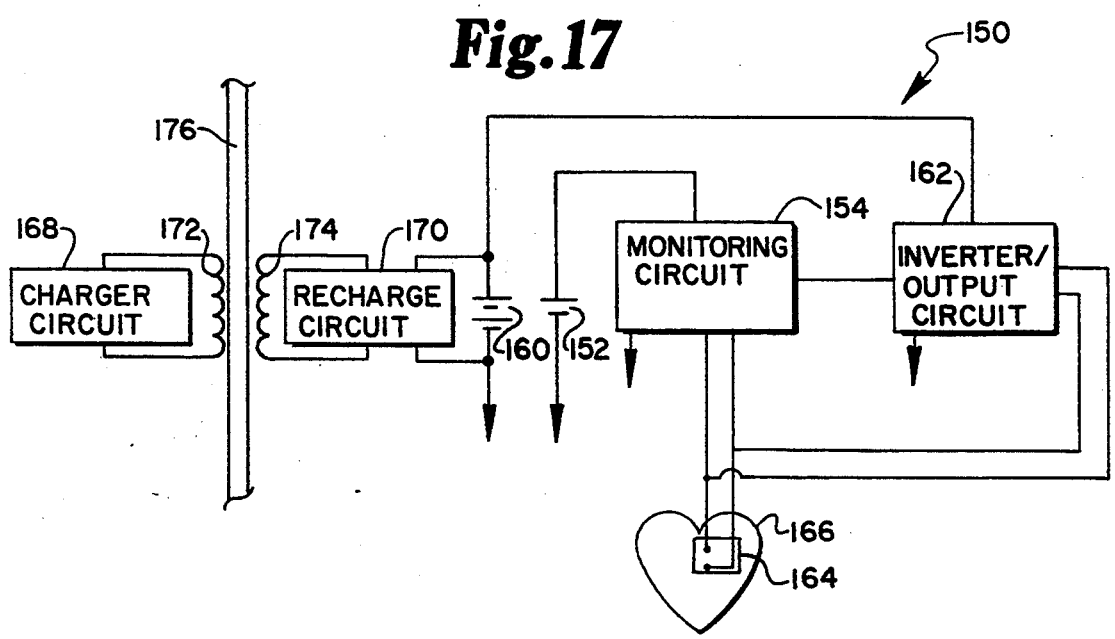
FIG. 17 is a block diagram of a rechargeable version of the dual battery system shown in FIG. 16.

FIG. 17 illustrates a dual battery system 150 for an ICD where the batteries are rechargeable. A battery 152 of appropriate voltage and minimum physical size connects to and powers a monitoring circuit 154 only. Another battery 160, which is rechargeable and of appropriate voltage and minimum physical size connects to and powers the capacitor-discharge output circuit 162 only. Charging of the battery 160 occurs by a radio frequency link between an external charger circuit 168 and an implanted recharge circuit 170. A coil 172 connects with the external charger circuit 168 and transmits RF energy from the coil 172 through the epidermis 176 where it is received by the implanted coil 174. The coil 174 supplies RF energy to the recharge circuit 170 so that the battery 160 may be charged. The dual battery system 150 operates and is sized in a manner similar to the dual battery system 130. In the dual battery system 150, the ICD has a finite and predictable monitoring life based upon the capacity of the primary pacing battery 152, and an infinite life for the output power surface battery 160 based on a theoretically perfect secondary rechargeable battery. Optionally, the battery 152 which powers the monitoring circuit 154 could also be rechargeable and would include another similar RF charging link as used for rechargeable battery 160.

Staged Energy Circuit with an Internally Rechargeable Battery

Figure 18:
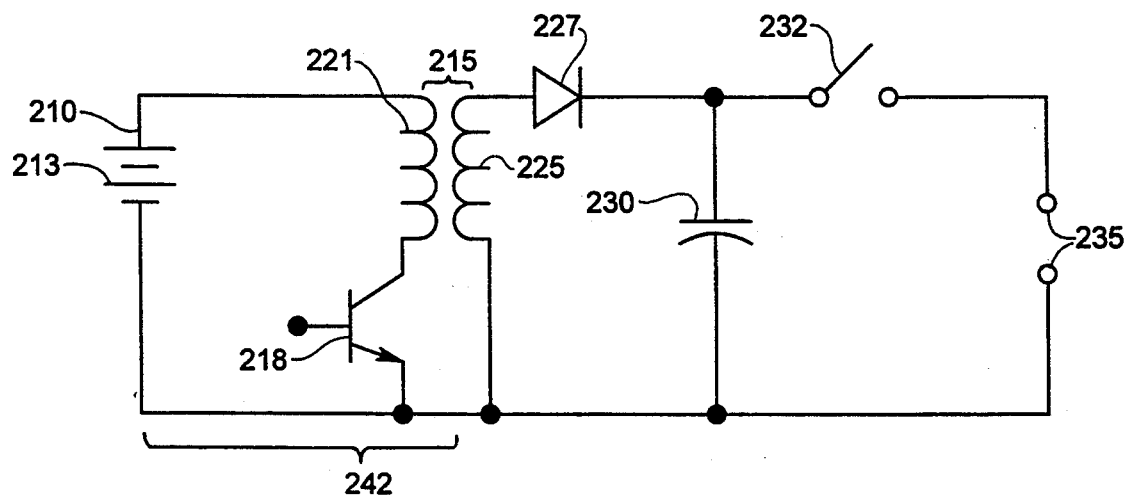
FIG. 18 is a simplified circuit diagram of a prior art implantable defibrillator circuit.

FIG. 18 is a simplified circuit diagram of a known implantable defibrillator circuit 210. Circuit 210 comprises a high current defibrillation battery 213, which is typically a lithium silver vanadium pentoxide (LiAgVO$_5$) battery. A high voltage transformer 215 comprises a transistor switch 218 which drives the primary 221. The oscillator driving switch 218 provides an alternating current through the primary of transformer 215. The secondary 225 of transformer 215 produces a significantly higher voltage which is rectified by diode 227 and stored in capacitor 230. When capacitor 230 is fully charged, the semiconductor switch 232 is activated to complete the circuit which delivers the charge of capacitor 230 to the cardiac electrodes 235 for defibrillation of the heart. A configuration which is similar to the above circuit comprises substitution of a H-bridge in place of switch 232. This permits delivery of the current from capacitor 230 in either polarity, which allows delivery of a biphasic pulse.

Figure 19:
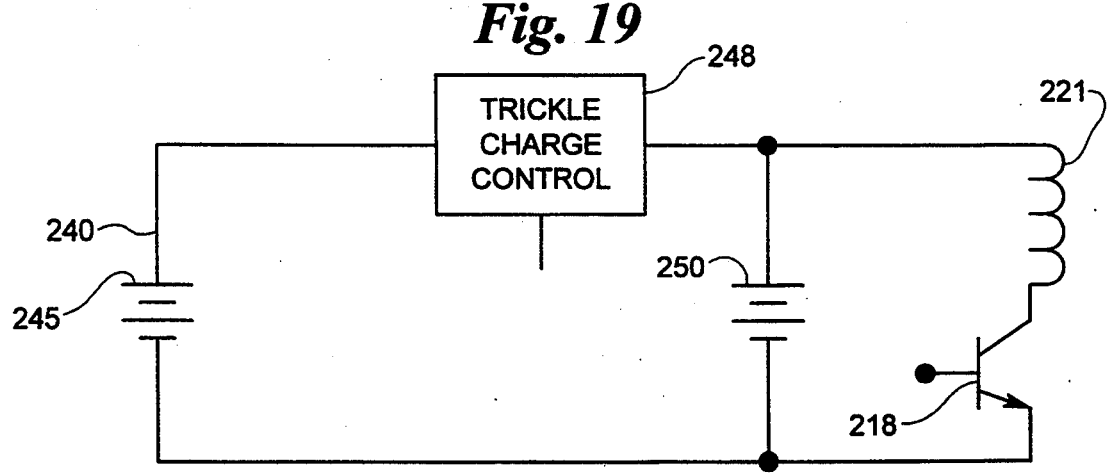
FIG. 19 is a simplified schematic circuit diagram of a staged energy concentration circuit of the preferred embodiment of the present invention.

FIG. 19 discloses a simplified schematic staged energy circuit 240. Circuit 240 comprises a first embodiment of an improved staged energy concentration means. Circuit 240 preferably comprises a first stage of energy concentration comprising a non-rechargeable battery, such as a high energy density pacing battery 245, configured for applying a small $\mu$Amp current to the trickle charge control circuitry 248. This provides an optimum current to be supplied to a second stage of energy concentration, comprising at least rechargeable battery means. The rechargeable battery means preferably comprises a rechargeable defibrillator battery 250 and is maintained fully charged by the pacing battery 245. Rechargeable defibrillator battery 250 is used to drive primary 221 of the high voltage transformer, or similar power transfer means, through a switch 218 in a manner similar to conventional circuits.

The staged energy concentration configuration of circuit 240 permits use of high density pacing batteries to store energy in combination with a very small rechargeable defibrillator battery to deliver a high current for up to about 10 shocks. A typical defibrillator will deliver about 200 defibrillator shocks. Assuming each of the shocks is less than 30 Joules as provided for by the present invention, and with transformer losses of 25%, the energy system must store 200×240 J32 8000 Joules. However, due to this staged energy arrangement, the rechargeable battery need only store enough energy for a typical cardiac defibrillation session of about 5 shocks in less than about four minutes. The four minute maximum for each defibrillation session is used because brain damage occurs if defibrillation is not successful in about four minutes. The battery means comprising the second stage of energy concentration must therefore only store about 5×240 J=200 Joules. Although this is very little energy, the second stage battery means must be able to deliver a fairly high current of about 1-2 Amps.

Figure 20:
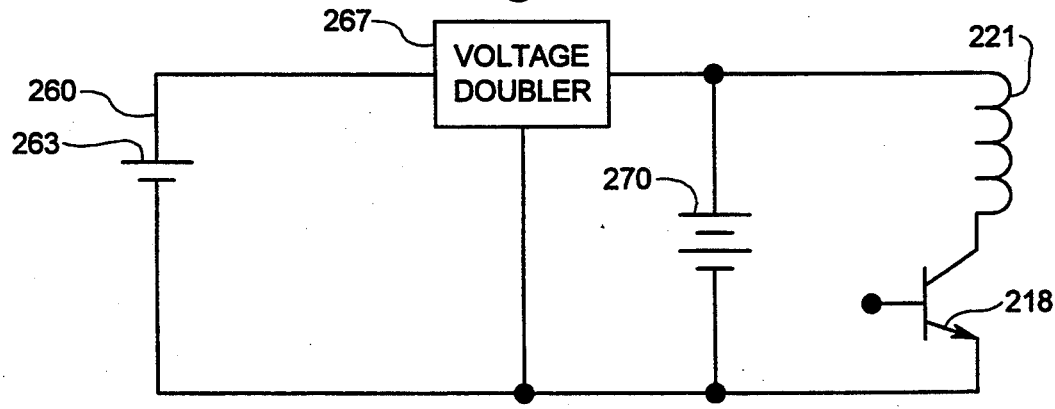
FIG. 20 is a simplified schematic circuit diagram of an alternate embodiment staged energy concentration circuit of FIG. 18.

FIG. 20 discloses another embodiment of the staged energy concentration invention. Circuit 260 discloses a single cell pacing battery 263 which is used to power a voltage doubler circuit 267. This doubler circuit 267, which comprises numerous embodiments, may be configured to produce an output of approximately 6 Volts for charging a rechargeable defibrillation battery, such as battery 270.

Figure 21:
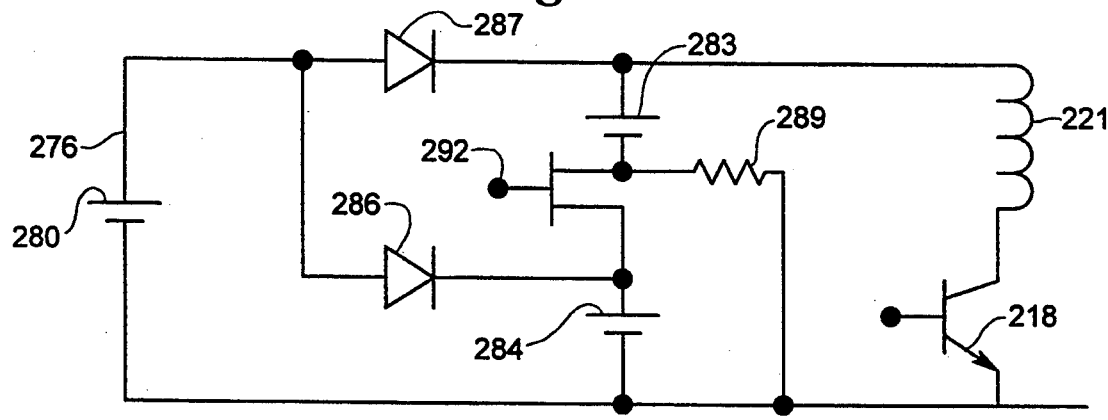
FIG. 21 is a simplified schematic circuit diagram of another alternate embodiment staged energy concentration circuit of FIG. 18

Another embodiment of a staged energy concentration defibrillator circuit is shown in FIG. 21, in which circuit 276 comprises first stage battery 280. Battery 280 is a low voltage, for example a 2.8 Volt, LiI single cell battery which charges two second stage batteries 283 and 284. Batteries 283, 284 are preferably Lithium Titanium Disulfide (LiTiS$_2$) batteries. Preferably, battery 284 is charged through diode 286, battery 283 is charged through diode 287, and resistor 289 is used with a preferred value of 10K Ohms. Field effect transistor switch 292 is off during this time. It is recognized that this schematic circuit is further simplified because there is optimal trickle charge current limiting between battery 280 and the two diodes, however, that detail is not considered important to this depiction of the invention.

When fibrillation is detected by related detection circuitry, it is then time to charge the defibrillation capacitor(s) and switch 292 is turned on. That places batteries 283 and 284 in series, providing a voltage of approximately 5 volts for the transformer primary 221. As above, oscillating switch 218 is used to cause a pulsating current to pass through primary 221 of the transformer.

Use of a multi-stage energy concentration defibrillator, as disclosed in FIGS. 19-21, provides great savings in both volume and weight of the defibrillator. For example, since the defibrillator battery chemistry has about half the density of the pacing battery, it is possible to reduce the total battery weight and volume by greater than about 50%. This provides dramatic improvement in the manufacture, implantation, and operation of the defibrillator, particularly in view of the restricted size of desired pectoral implant sites.

The invention further comprises a multi-stage energy concentration technique for a defibrillator in which the defibrillator capacitor means comprises either a third stage or a secondary sub-circuit of the second stage. In either configuration, it is advantageous to provide a rechargeable second stage or intermediate battery means as a fully charged high current output battery means. This permits rapid charging of the defibrillator capacitor means. Indeed, in certain configurations it is now possible to recharge at a rapid 3-5 second rate using this invention rather than at a slower rate, which is common in the industry. Therefore, yet another advantage of this invention derives from the use of the second stage energy concentration as a recharge rate accelerator. This also results in a defibrillator with reduced end of life charge degradation due to the constantly recharged second stage. This feature effectively provides a battery life extension capability before elective replacement, assuming certain accepted energy levels.

Intensifying Battery

Figure 22:
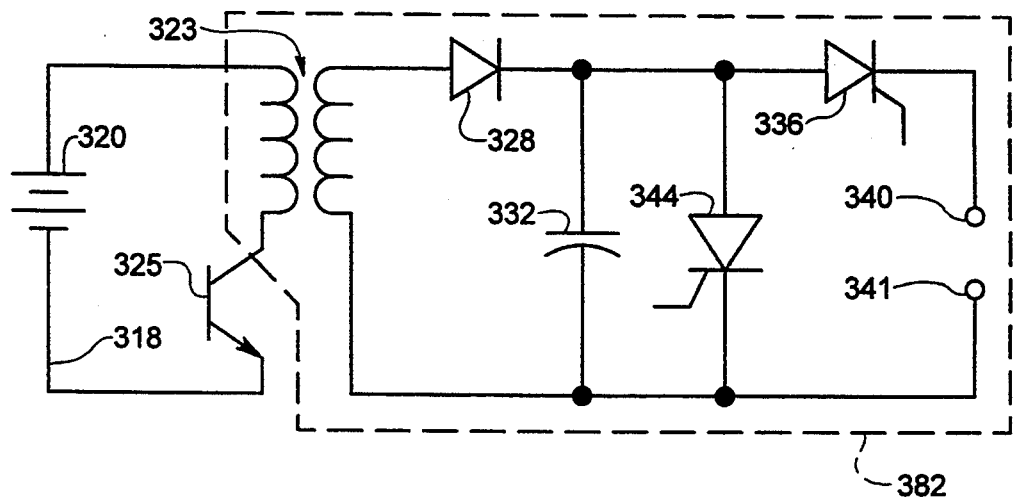
FIG. 22 is a schematic circuit diagram illustrating representative prior art circuitry for an implantable cardioverter defibrillator.

FIG. 22 illustrates representative circuitry for generating a monophasic defibrillation pulse in the prior art. Circuit 318 comprises battery 320 which is used to provide a current through the primary winding of transformer 323. The current is cycled on and off at a high rate of speed by switching transistor 325. The output from transformer 323 is rectified by diode 328 and is captured in the main storage capacitor 332. In order to deliver the pulse to the heart, silicon controlled rectifier 336 is triggered providing a current path from capacitor 323 to the electrodes 340, 341 in the heart. At the point of pulse truncation at the end of time period T$_1$, silicon controlled rectifier 344 is triggered. This quickly discharges capacitor 332 and back biases silicon controlled rectifier 336 to shut off the flow of current through electrodes 340, 341 to the heart.

Biphasic and multiple pulse defibrillation countershock have been experimented with for many years. Ventricular defibrillation of dogs with waves comprising two pulses with a pulse length and pulse interval adjusted so that those cells excitable at any moment are defibrillated by the first pulse and are refractory to the second pulse was disclosed by Kugelberg as early as October 1965, in the Scandinavian Society of Thoracic Surgery, pages 123-128. Kugelberg considered a variety of pulses and spacings and found that ventricular defibrillation was indeed quite possible with multiple pulses. U.S. Pat. No. 4,996,984, issued to Sweeney, discloses adjusting the timing between multiple bursts of defibrillation energy based upon the fibrillation cycle length of the mammal. Similarly, Sweeney and Reid disclose that the interaction between multiple pulses is non-linearly related to the fibrillation cycle length, and that the spacing between multiple pulses may be a fixed percentage of the spacing between fibrillation zero crossings in the heart. (II-610, Supplement II Circulation, Vol. 84, No. 4, October 1991, No. 2425). Johnson et al disclose that successive biphasic shocks delivered through two different electrodes may be either beneficial or detrimental depending on the delay between the two shocks. (NASPE Abstracts, April 1991, Part II, no. 391; PACE, Vol. 14, p. 715). Other examples of multiple pulse defibrillation systems include U.S. Pat. Nos. 5,107,834 to Ideker et al and 4,708,145 to Tacker, Jr. et al.

In principal, the above disclosures demonstrate that the energy per pulse in a multiple or closely spaced pulse technique using different pathways, multiple defibrillators, or other inefficient means of energy generation and distribution, may be reduced from what is commonly used in a single monophasic or widely spaced pulse technique. Thus, it can be seen that a multiple pulse waveform might lower the total defibrillation energy threshold by up to 50 percent. However, such a system requires multiple sizeable capacitors. The intermediate power intensifier as disclosed below teaches means for overcoming the impediments of the theoretical multiple pulse systems. Also disclosed is a novel means for providing a rapid pulse power system for use with conventional ICD circuits to permit optional prompt transition from a widely spaced defibrillation pulse sequence to a closely spaced defibrillation pulse sequence.

The energy generation problem is appreciated more fully by calculating the charging power required of a representative capacitor system in an ICD device. Assuming a conventional monophasic defibrillator which is designed to deliver a 30 Joule countershock, a 12 second delay for capacitor charging is considered acceptable after fibrillation is detected. The charging power is described by simple calculation of 30 Joules divided by 12 seconds, which yields about 3 watts. This 3 watt level of power is available from high quality defibrillation primary cells, such as lithium silver vanadium pentoxide cells, although others may be suitable.

Assuming a use of two closely spaced pulses, defibrillation could occur with 15 Joules in each pulse. The capacitor could be designed to store only 15 Joules and could be made of only half the size of present capacitors. However, although the capacitor has 12 seconds to charge in order to create the first pulse by use of present circuitry, the capacitor then must be quickly recharged to provide the second pulse. Generally, the amount of time required to quickly recharge is the same time as that required for optimum spacing between the two pulses, which is about 0.25 seconds. Therefore, the charging power must be equal to 15 Joules divided by 0.25 seconds. This requires a 60 watt power source. Currently, there is no functional implantable battery which is capable of providing such power output.

Figure 23:
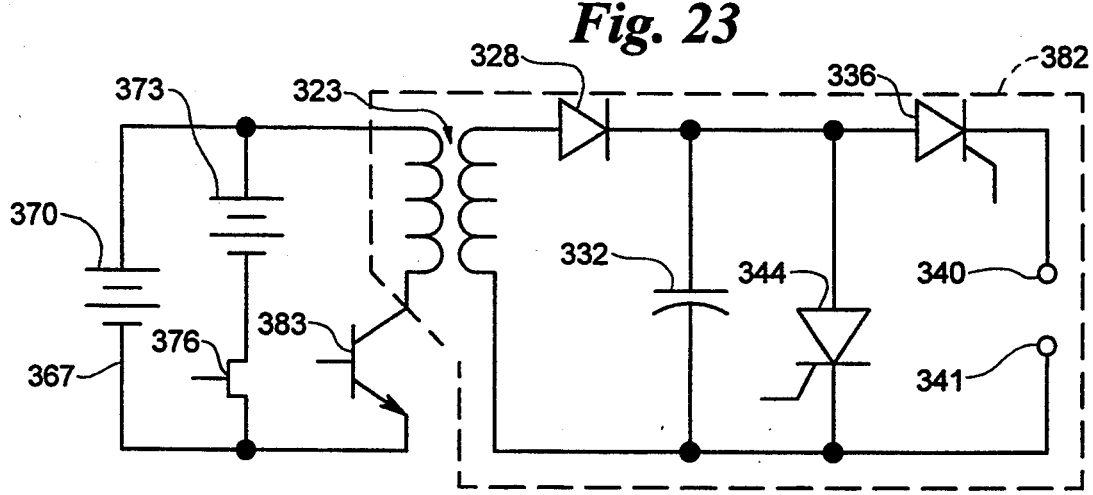
FIG. 23 is a schematic circuit diagram of one embodiment of the implantable cardioverter defibrillator rapid pulse circuitry of the preferred embodiment of the present invention.

FIG. 23 discloses the essential circuit elements of one embodiment of the present invention in which circuit 367 uses both a primary battery and an intermediate power intensifying battery, with the latter comprising a very high power output battery to provide the high charging power between capacitor pulses. As shown, battery 370 is a low amperage primary defibrillation cell, which is preferably a lithium silver vanadium pentoxide type, although other materials are feasible. When fibrillation is detected, battery 370 is used to quickly charge a rechargeable battery 373 which is capable of very high power output. This is preferably accomplished through the use of transistor switch 376. Battery 373 is preferably selected from a list of possible high power rechargeable batteries, such as a lithium titanium disulfide, lithium sulphur dioxide, or others suitable for producing the desired power in a rechargeable configuration. When battery 373 has been sufficiently charged then it is useful as a source of high current charging power to capacitor 332 in circuitry sub-section 382, shown in circuit 318 of Fig. 22 and in circuit 367 of FIG. 23.

The difference between the capacitor charging circuitry of FIG. 23 and FIG. 22 is an approximately 20:1 charging power ratio of 60 watts rather than 3 watts. The charging circuitry shown as schematic circuit 367 provides power means for recharging the capacitor of the related ICD device, after an initial discharge, between subsequent multiple pulses. This eliminates additional capacitors and eliminates about half of the capacitor volume of known ICD devices. The invention also results in significant improvement in size and operation of an ICD device.

Figure 24:
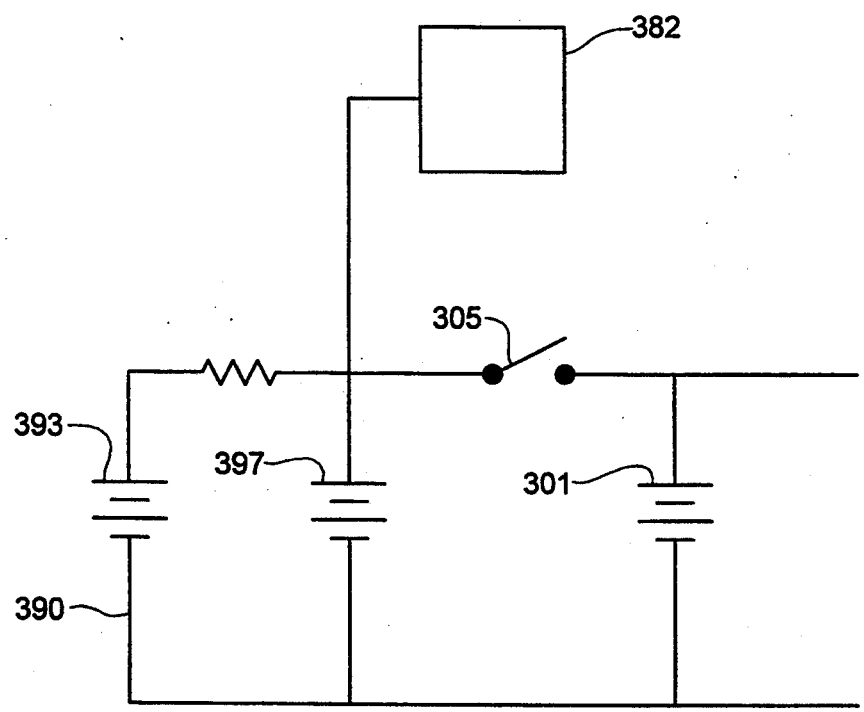
FIG. 24 is a schematic circuit diagram of another embodiment of the implantable cardioverter defibrillator rapid pulse circuitry of FIG. 23.

Another alternate embodiment for charging rechargeable battery 73 after fibrillation is detected is disclosed in FIG. 24. In this embodiment, circuit 390 comprises a relatively low amperage, e.g. milliamps, primary defibrillation battery 393. One example of such a battery 393 comprises a pacing type lithium iodide battery, although other materials are also suitable. Circuit 390 also comprises high power output (approximately 1–3 Amps) intermediate power intensifying battery 397. A preferred battery 397 comprises a lithium titanium di-sulfide battery. Battery 301 comprises a very high amperage (10–30 amps) battery. In operation, circuit 390 allows continuous trickle charge from battery 393 to battery 397. This maintains battery 97 in a substantially fully charged configuration until detection of fibrillation. After detection of fibrillation, battery 397 simultaneously charges the main energy delivery capacitor 332 within sub-section 382 and battery 301, via switch 305. Capacitor 332 then discharges and is again re-charged with battery 397. However, battery 397 is not normally able to fully charge capacitor 332 in less than at least about 5 seconds. In a closely spaced multiple pulse ICD device power system it is necessary to provide means other than battery 397 to provide charging power for subsequent pulses to the heart. Rather than providing multiple charging pathways or a plurality of capacitors, circuit 90 discloses use of battery 301 to provide high amperage high power means for charging a :main energy delivery capacitor for countershock pulses after the initial countershock/pulse.

The embodiment of circuits 367 and 390 are each also advantageous as a rapid pulse power system for use with implantable cardioverter devices. This rapid pulse power system may be integrated into other known or proprietary circuits as a means of enabling rapid and optional transition from a widely spaced defibrillation pulse sequence to a closely spaced defibrillation pulse sequence. This is accomplished without adding any additional capacitors, which would detract from the size and volume advantages of the invention.

Optimized Battery Budget

Budgeting the $E_t$ for the preferred embodiment of the ICD of the present invention, it will first be noted that the lower maximum $E_c$ of the present invention produces a minimum charging time ($t_{min}$) of 8.5 seconds, in contrast to the 12 second minimum in the prior art devices. The use of the improvements to the battery system as previously set forth allows the idle current $I_i$ and the pacing current $I_p$ to be reduced by about half to about 10 μAmps and 3.5 μAmps, respectively, as compared to about 20 μAmps and 7 μAmps in the prior art devices. By reducing the budgeted number of countershock $N_p$ to about 150, rather than 200, it will be seen that the $E_t$ of the preferred embodiment is effectively reduced in half as compared to the prior art devices.

$$E_t = ((I_b * t_c) * N_p) + (I_i * l) + (I_p * l) \quad \text{(Eq. 33)}$$
$$= ((8.5 \text{ Amp-sec}) * 150) + (10 \mu A * 5 \text{ years}) + (3.5 \mu A * 5 \text{ years})$$
$$= (0.35 \text{ Amp-hours}) + (0.45 \text{ Amp-hours}) + (0.15 \text{ Amp-hours})$$
$$= 1.0 \text{ Amp-hours}$$

Although the description of the preferred embodiment has been presented, it is contemplated that various changes could be made without deviating from the spirit of the present invention. Accordingly, it is intended that the scope of the present invention be dictated by the appended claims, rather than by the description of the preferred embodiment.

What is claimed is:

1. An implantable cardioverter defibrillator for subcutaneous positioning within a human patient comprising:

a sealed housing structure constructed of a biocompatible material and having a displacement volume of less than about 90 cc;

one or more connector port means, each connector port means disposed in a wall of said housing structure for providing electrical connections between an interior space of said housing structure and a corresponding electrode lead within said human patient;

circuit means disposed within said interior space of said housing structure and operably connected to said connector port means for sensing cardiac signals received from one or more of said electrode leads and, in response to the detection of an arrhythmia in said cardiac signals, controlling delivery of one or more high energy electrical cardioversion/defibrillation countershocks of at least 0.5 Joules to the myocardium of said human patient;

capacitor means disposed within said interior space of said housing structure and operably connected to said circuit means for storing electrical energy to generate said electrical cardioversion/defibrillation countershocks and having an effective capacitance value of less than 120 μF; and battery means disposed within said interior space of said housing structure and operably connected to said circuit means and said capacitor means for providing electrical energy to said circuit means and said capacitor means, wherein said battery means and said capacitor means are selected such that a maximum electrical charge energy stored by said capacitor means for each of said electrical cardioversion/defibrillation countershocks is less than about 30 J and said implantable cardioverter defibrillator is capable of delivering at least five of said electrical cardioversion/defibrillation countershocks in a four minute period.

2. The implantable cardioverter defibrillator of claim 1 wherein said circuit means controls the delivery of said electrical cardioversion/defibrillation countershocks such that a pulse duration of a monophasic one of said cardioversion/defibrillation countershocks, or of a first phase of a multiphasic one of said cardioversion/defibrillation countershock is less than about 6 milliseconds.

3. The implantable cardioverter defibrillator of claim 2 wherein the duration of each of said electrical cardioversion/defibrillation countershocks is determined by said circuit means to be the sum of:

a first value derived from a first predetermined percentage of an RC time constant, with R being a myocardial tissue resistance value and C being said effective capacitance value of said capacitor means; and a second value derived from a second predetermined percentage of a cardioversion chronaxie, $d_c$, value.

4. The implantable cardioverter defibrillator of claim 3 wherein said first and second predetermined percentages are between 0.5 and 0.65.

5. The implantable cardioverter defibrillator of claim 4 wherein said first and second predetermined percentages are both 0.58.

6. The implantable cardioverter defibrillator of claim 3 wherein said first value is determined by comparing an output voltage of said electrical cardioversion/defibrillation countershock with said first predetermined percentage and said second value is determined by providing for a fixed time period equal to said second value.

7. The implantable cardioverter defibrillator of claim 2 wherein at least one of said electrical cardioversion/defibrillation countershocks is a biphasic pulse having a positive phase and negative phase.

8. The implantable cardioverter defibrillator of claim 7 wherein the duration of the positive phase and negative phase are equal and is determined by said circuit means to be the sum of:

a first value derived from a first predetermined percentage of an RC time constant, with R being a myocardial tissue resistance value and C being said effective capacitance value of said capacitor means; and a second value derived from a second predetermined percentage of a cardioversion chronaxie, $d_c$, value.

9. The implantable cardioverter defibrillator of claim 1 wherein said battery means is capable of charging said capacitor means to said maximum charge amount in less than about 10 seconds.

10. The implantable cardioverter defibrillator of claim 1 wherein said battery means has an estimated life of five years and a total storage capacity of less than about 1.0 Amp-hours.

11. The implantable cardioverter defibrillator of claim 1 wherein an optimum capacitance value (C) for said effective capacitance value of said capacitor means is determined by the simultaneous solution of the equations:

$$E_c = 0.5 C V_d^2$$

$$C = 0.8 d_c / R$$

where $E_c$ is said maximum charge amount, $V_d$ is a maximum voltage for each of said electrical cardioversion/defibrillation countershocks, $d_c$ is a cardioversion chronaxie value and R is a myocardial tissue resistance value.

12. The implantable cardioverter defibrillator of claim 1 wherein said battery means comprises:
a first battery means for providing electrical power to said circuit means to monitor said cardiac signals; and
a second battery means, separate from said first battery means and having different energy storage characteristics, for providing electrical power to charge said capacitor means to generate said electrical cardioversion/defibrillation countershocks.

13. The implantable cardioverter defibrillator of claim 12 wherein said second battery means is a rechargeable battery and further include charging circuitry for charging said rechargeable battery from said first battery means or from an external RF power source.

14. The implantable cardioverter defibrillator of claim 1 wherein said battery means comprises:
a low power output primary battery;
a high power output intermediate power intensifying battery; and
switch means connected to said primary battery and said intermediate power intensifying battery for permitting said intermediate power intensifying battery to rapidly charge said capacitor means,
such that said capacitor means discharges in a first pulse an electrical charge derived from said primary battery and discharges one or more subsequent pulses of electrical charge derived from said intermediate power intensifying battery to permit the implantable cardioverter defibrillator to deliver multiple closely spaced cardioversion/defibrillation countershocks.

15. The implantable cardioverter defibrillator of claim 1 wherein said displacement value of said housing structure is greater than about 40cc and less than about 60cc.

16. The implantable cardioverter defibrillator of claim 1 wherein the total weight of said implantable cardioverter defibrillator is less than about 120 grams.

17. The implantable cardioverter defibrillator of claim 1 wherein said housing structure has a length to width to thickness ratio of approximately 5 to 3 to 1.

18. An implantable cardioverter defibrillator for subcutaneous positioning within the pectoral region a human patient comprising:
a sealed housing structure constructed of a biocompatible material and having a displacement volume of less than about 90cc;
one or more connector port means, each connector port means disposed in a wall of said housing structure for providing electrical connections between an interior space of said housing structure and a corresponding electrode lead within said human patient;
circuit means disposed within said interior space of said housing structure and operably connected to said connector port means for sensing cardiac signals received from one or more of said electrode leads and, in response to the detection of an arrhythmia in said cardiac signals, controlling delivery of one or more electrical cardioversion/defibrillation countershocks of at least 0.5 Joules to the myocardium of said human patient;
capacitor means disposed within said interior space of said housing structure and operably connected to said circuit means for storing electrical energy to generate said electrical cardioversion/defibrillation countershocks; and
battery means disposed within said interior space of said housing structure and operably connected to said circuit means and said capacitor means for providing electrical energy to said circuit means and said capacitor means,
wherein said battery means and said capacitor means are selected to maximize a physiologically effective current ($I_{pe}$) for a maximum electrical charge energy ($E_c$) stored by said capacitor means.

19. The implantable cardioverter defibrillator of claim 18 wherein said physiologically effective current ($I_{pe}$) is determined by solution of the equation:

$$I_{pe} = (I_{ave} * d)/(d_c + d)$$

where $I_{ave}$ is an average current of said electrical cardioversion/defibrillation countershocks, d is a duration of said electrical cardioversion/defibrillation countershocks, and $d_c$ is a cardioversion chronaxie value.

20. An implantable cardioverter defibrillator for subcutaneous positioning within the pectoral region of a human patient comprising:
a sealed housing structure constructed of a biocompatible material and having a displacement volume of less than about 90 cc and including one or more connector ports disposed in a wall of said structure for providing electrical connections between an interior space of said structure and electrode leads in said patient;
circuit means within said interior space for sensing cardiac signals received from said electrode leads and, in response to the detection of an arrhythmia in said cardiac signals, controlling delivery of one or more electrical cardioversion/defibrillation countershocks of at least 0.5 Joules to said patient;
capacitor means within said interior space for storing electrical energy to generate said electrical cardioversion/defibrillation countershocks and having an effective capacitance of less than about 120 μF; and
battery means within said interior space for providing electrical energy to said circuit means and said capacitor means and capable of charging said capacitor means in less than about 10 seconds to a maximum electrical charge energy of less than about 30 Joules.

21. An implantable cardioverter defibrillator for subcutaneous positioning within a pectoral region of a human patient comprising:
a sealed housing structure constructed of a biocompatible material and having a displacement volume of less than about 90 cc;
one or more connector ports, each connector port disposed in a wall of the housing structure for providing electrical connections between an interior space of the housing structure and a corresponding electrical lead that is implanted within the human patient; and
circuit means disposed within the interior space of the housing structure and operably connected to the connector ports and responsive to a cardiac signal received from the human patient via one or more of the electrical leads for detecting an arrhythmia in the cardiac signal and, in response, controlling delivery of one or more high energy electrical cardioversion/defibrillation countershocks of at least 0.5 joules to the human patient.

22. The implantable cardioverter defibrillator of claim 21 wherein the displacement value of the housing structure is greater than about 40 cc and less than about 60 cc.

23. The implantable cardioverter defibrillator of claim 21 wherein a total weight of the implantable cardioverter defibrillator is less than about 120 grams.

24. The implantable cardioverter defibrillator of claim 21 wherein the housing structure has a length to width to thickness ratio of approximately 5 to 3 to 1.

25. The implantable cardioverter defibrillator of claim 21 wherein the circuit means comprises:
- detection means for receiving the cardiac signal and detecting the arrhythmia;
- capacitor means for storing electrical energy to generate the electrical cardioversion/defibrillation countershocks;
- battery means for providing electrical energy to the detection means, the control means and the capacitor means; and
- control means for controlling storing of the electrical energy in the capacitor means and discharging of the electric energy in the capacitor means as the one or more high energy electrical cardioversion/defibrillation countershocks.

26. The implantable cardioverter defibrillator of claim 25 wherein a maximum electrical charge energy stored by the capacitor means for each electrical cardioversion/defibrillation countershocks is less than about 30 joules.

27. The implantable cardioverter defibrillator of claim 26 wherein the battery means charges the capacitor means to the maximum electrical charge energy in less than about 10 seconds.

28. The implantable cardioverter defibrillator of claim 25 wherein the battery means has a total energy storage capacity of less than 1.0 amp-hours.

29. The implantable cardioverter defibrillator of claim 25 wherein the capacitor means has an effective capacitance value of less than 120 $\mu$F.

30. The implantable cardioverter defibrillator of claim 29 wherein the effective capacitance value of the capacitor means is an optimum capacitance value (C) determined by the simultaneous solution of the equations:

$$E_c = 0.5 C V_d^2$$

$$C = 0.8 d_c / R$$

where $E_c$ is said maximum charge amount, $V_d$ is a maximum voltage for each electrical cardioversion/defibrillation countershock, $d_c$ is a cardioversion chronaxie value and R is a myocardial tissue resistance value.

31. The implantable cardioverter defibrillator of claim 25 wherein the control means controls the delivery of the electrical cardioversion/defibrillation countershocks such that a pulse duration of a monophasic one of the cardioversion/defibrillation countershocks, or of a first phase of a multiphasic one of the cardioversion/defibrillation countershocks is less than about 6 milliseconds.

32. The implantable cardioverter defibrillator of claim 31 wherein the duration of each electrical cardioversion/defibrillation countershocks is determined by the control means to be the sum of:
- a first value derived from a first predetermined percentage of an RC time constant, with R being a myocardial tissue resistance value and C being an effective capacitance value of the capacitor means; and
- a second value derived from a second predetermined percentage of a cardioversion chronaxie, $d_c$, value.

33. The implantable cardioverter defibrillator of claim 32 wherein the first and second predetermined percentages are between 0.5 and 0.65.

34. The implantable cardioverter defibrillator of claim 33 wherein the first and second predetermined percentages are both 0.58.

35. The implantable cardioverter defibrillator of claim 32 wherein the first value is determined by comparing an output voltage of the electrical cardioversion/defibrillation countershock with a first predetermined percentage and the second value is determined by providing for a fixed time period equal to said second value.

36. The implantable cardioverter defibrillator of claim 32 wherein at least one of the electrical cardioversion/defibrillation countershocks is a biphasic pulse having a positive phase and negative phase.

37. The implantable cardioverter defibrillator of claim 36 wherein a duration of the positive phase and negative phase are equal and is determined by the control means to be the sum of:
- a first value derived from a first predetermined percentage of an RC time constant, with R being a myocardial tissue resistance value and C being an effective capacitance value of the capacitor means; and
- a second value derived from a second predetermined percentage of a cardioversion chronaxie, $d_c$, value.

38. The implantable defibrillator of claim 25 wherein a ratio of a physiologically effective current ($I_{pe}$) to a maximum stored energy charge ($E_c$) of the capacitor means is at least about 20%.

* * * * *